United States Patent
Pyun et al.

(10) Patent No.: US 12,291,584 B2
(45) Date of Patent: May 6, 2025

(54) CHALCOGENIDE HYBRID INORGANIC/ORGANIC POLYMERS (CHIPS) FOR INFRARED OPTICAL MATERIALS AND DEVICES

(71) Applicant: ARIZONA BOARD OF REGENTS ON BEHALF OF THE UNIVERSITY OF ARIZONA, Tucson, AZ (US)

(72) Inventors: Dong-Chul Pyun, Tucson, AZ (US); Robert A. Norwood, Tucson, AZ (US); Roland Himmelhuber, Tucson, AZ (US); Tristan Stephen Kleine, Tucson, AZ (US); Liliana Ruiz Diaz, Tucson, AZ (US); Laura E. Anderson, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 70 days.

(21) Appl. No.: 18/143,562

(22) Filed: May 4, 2023

(65) Prior Publication Data
US 2023/0272130 A1    Aug. 31, 2023

Related U.S. Application Data

(62) Division of application No. 16/499,689, filed as application No. PCT/US2018/025178 on Mar. 29, 2018, now Pat. No. 11,685,797.

(60) Provisional application No. 62/488,451, filed on Apr. 21, 2017, provisional application No. 62/480,403, filed on Apr. 1, 2017, provisional application No. 62/480,404, filed on Apr. 1, 2017.

(51) Int. Cl.
| | | |
|---|---|---|
| C08F 112/14 | (2006.01) | |
| C07C 329/10 | (2006.01) | |
| G02B 1/04 | (2006.01) | |

(52) U.S. Cl.
CPC .......... *C08F 112/30* (2020.02); *C07C 329/10* (2013.01); *G02B 1/04* (2013.01)

(58) Field of Classification Search
CPC .............................. C08F 112/30; C07C 329/10
See application file for complete search history.

(56) References Cited

U.S. PATENT DOCUMENTS

| | | |
|---|---|---|
| 4,929,694 A | 5/1990 | Aslam et al. |
| 2002/0021878 A1 | 2/2002 | Allan et al. |
| 2003/0189758 A1 | 10/2003 | Baer et al. |
| 2009/0208719 A1 | 8/2009 | Kang et al. |
| 2009/0301896 A1 | 12/2009 | Tour et al. |
| 2011/0042589 A1 | 2/2011 | Norwood et al. |

(Continued)

FOREIGN PATENT DOCUMENTS

| | | |
|---|---|---|
| WO | WO-2017/011533 A1 | 1/2017 |
| WO | WO-2017/187279 A1 | 11/2017 |

OTHER PUBLICATIONS

International Search Report and Written Opinion in International Patent Application PCT/US2018/025178 dated Jul. 11, 2018.

(Continued)

*Primary Examiner* — Catherine S Branch
(74) *Attorney, Agent, or Firm* — Foley & Lardner LLP

(57) ABSTRACT

The present invention provides certain polymeric materials, precursors thereof as well as the preparation and uses thereof.

10 Claims, 12 Drawing Sheets

(56) References Cited

U.S. PATENT DOCUMENTS

2014/0199592 A1    7/2014  Pyun et al.

OTHER PUBLICATIONS

Kricheldorf, "Polymerization of Si-Containing Vinyl Monomers and Acetylenes", Silicon in Polymer Synthesis (Kricheldorf, ed.) 1996 (Year: 1996).
PubChem CID=118347463. Create date Feb. 23, 2016 (Feb. 23, 2016) pp. 1-9, see entire document, especially p. 3.

TEM Grid

CHALCOGENIDE HYBRID INORGANIC/ORGANIC POLYMERS (CHIPS) FOR INFRARED OPTICAL MATERIALS AND DEVICES

CROSS-REFERENCE TO RELATED APPLICATIONS

This application is a divisional of U.S. patent application Ser. No. 16/499,689, filed on Sep. 30, 2019, which is the U.S. National Stage of International Application No. PCT/US2018/025178, filed on Mar. 29, 2018, and which claims the benefit of priority to U.S. Provisional Appl. No. 62/480,403, filed Apr. 1, 2017; U.S. Provisional Appl. No. 62/488,451, filed Apr. 21, 2017; and U.S. Provisional Appl. No. 62,480,404, filed Apr. 1, 2017, the contents of all of which are incorporated by reference herein in their entirety.

GOVERNMENT SUPPORT

This invention was made with government support under Grant No. 1607971 awarded by NSF. The government has certain rights in the invention.

FIELD OF THE INVENTION

The present invention is directed to polymeric materials, the use thereof, and the preparation thereof.

BACKGROUND OF THE INVENTION

This background information is provided for the purpose of making information believed by the applicant to be of possible relevance to the present invention. No admission is necessarily intended, nor should it be construed, that any of the preceding information constitutes prior art against the present invention.

An incredible abundance of elemental sulfur ($S_8$), nearly 7-million tons, is generated as a waste byproduct from hydrodesulfurization of crude petroleum feedstocks, which converts alkanethiols and other (organo) sulfur compounds into $S_8$. Before the invention of the inverse vulcanization process, there were only a limited number of synthetic methods available to utilize and modify elemental sulfur. Current industrial utilization of elemental sulfur is centered around sulfuric acid, agrochemicals, and vulcanization of rubber. For example, elemental sulfur is used primarily for sulfuric acid and ammonium phosphate fertilizers, where the rest of the excess sulfur is stored as megaton-sized, above ground sulfur towers.

While sulfur feedstocks are plentiful, sulfur is difficult to process. In its original form, elemental sulfur consists of a cyclic molecule having the chemical formulation $S_8$. Elemental sulfur is a brittle, intractable, crystalline solid having poor solid state mechanical properties, poor solution processing characteristics, and there is a limited slate of synthetic methodologies developed for it. Hence, there is a need for the production of new materials that offer significant environmental and public health benefits to mitigate the storage of excess sulfur in powder, or brick form.

Development of polymeric materials for infrared (IR) optical applications has not been achieved due to challenges in designing systems with sufficiently high refractive index (n) and transparency in the IR spectral regime. High refractive index polymers (HRIPs) are largely found in optical devices, such as lenses. These HRIPs offer several significant advances over older and current technologies in this field, such as lower densities, greater strengths, and overall increased performance. A higher "n" value indicates larger refractive power, and polymers tend to have greater resistance to damage and breakage. Lenses based on high n materials have reduced optical path lengths compared to their low n counterparts, hence resulting in reduced size and weight. For example, HRIPs allow for the production of thin lenses, even for high prescriptions, with refractive indices generally ranging from n=1.5 to n=1.8. Further, an increasing n value allows for lighter, more efficient frames (scopes) for these lenses. To date, organic plastics exhibit poor performance in the optical window from 1 to 10 µm due to strong IR absorption from the plastic material, deriving largely from C—H bonds. IR optical technology has numerous potential applications in the civil, medical, and military areas, where inorganic semiconductors (e.g., Ge, Si) and chalcogenide glasses have been widely used as materials for device components due to their high refractive indices (n~2.0-4.0) and low losses from 1-10 µm. Other examples of glass materials currently in use are InSb, InGaAs, HgCdTe, AsSe, and AsS. While such materials are well-suited for these applications, they are inherently more expensive, toxic, and difficult to process in comparison to organic or organic/Inorganic hybrid polymeric materials.

Sulfur has an inherently high refractive index (n~1.9-2.0), which is significantly higher than all organic plastic materials. Moreover, S—S bonds are largely IR inactive in this same optical window. Therefore, it is desirable to use elemental sulfur as the chemical feedstock for these materials due to both the low cost of $S_8$ and favorable optical properties. However, sulfur is inherently difficult to process into films and molded objects, and previous synthetic methods have limited abilities to incorporate sulfur and create polymers with a high content of S—S bonds. There remains a need to improve the optical properties of these polymers to enable the development of these types of materials for mid-IR applications.

The inventors have previously developed a facile, one-step polymerization termed "inverse vulcanization" to prepare sulfur polymers with a very high content of S—S bonds in the polymer backbone ranging from 50-90 wt % sulfur that exhibit both high refractive index (n=1.9 to 1.7 from 600-1500 nm) and high IR transparency, in which further details can be found in co-owned U.S. Pat. Nos. 9,567,439 and 9,306,218, the specifications of which are incorporated herein in their entirety by reference. The use of elemental sulfur as the chemical feedstock for these materials was desirable due to both the low cost of $S_8$ and favorable optical properties. However, to enable the development of these types of materials for mid-IR applications, there remains a need to improve the optical properties of these polymers.

Currently, chalcogenide glasses are a primary material of choice for IR optics (in addition to germanium) in the 3-5 micron wavelength range since all organic polymers strongly absorb in the IR optical regime. The chalcogenide-based polymers of the present invention exhibit superior processing advantages over chalcogenide glasses since the chalcogenide-based polymer may be solution or melt processed at relatively lower temperatures and generally lack highly toxic elements such as arsenic.

Chalcogenide-based polymers can utilize selenium to enhance the optical properties. The polymerization of liquid $S_8$ with elemental selenium ($Se_8$) and/or cyclic selenium sulfides to form the chalcogenic sulfur polymer greatly increases the refractive index of said polymers. As used herein, the chalcogenic sulur polymer may be referred to as chalcogenic hybrid inorganic/organic polymers (CHIPs).

Using the inverse vulcanization method, CHIPs are shown to be a viable comonomer to prepare chemically stable polymer plastic materials with tunable optical and thermochemical properties. Furthermore, the CHIPs may be fabricated into useful optical devices, such as films, waveguides, dielectric mirrors, Bragg reflectors, reflective coatings for the infrared (IR), molded (nano-, micro-) objects and lenses.

Additionally, for telecommunication applications, there is a demand for optical polymers that, upon exposure to UV or visible light, can allow for modulation of the refractive index. Optical polymers with this feature can be used to create integrated optical junctions, such as waveguides and interconnects, using low cost processing methods, such as solution processing, to couple different optical components in an integrated optical system. There currently remains a need for an optical polymer with these characteristics.

This large technological motivation for optical polymers that are low-cost and have variable refractive index led to the design and synthesis of a novel organic compound of the present invention. The organic compound incorporates functional groups in the molecule that allow for photoprocessing and that can be polymerized to produce new optical polymers having an increased refractive index upon removal of a BOC protecting group. The amenability of these materials to traditional optoelectronic processing methods (i.e., photolithography) allows for these materials to be deployed for the fabrication of new optical devices.

Finally, photonic crystals are generally defined as materials with a spatial periodicity in their refractive index (n). Photonic crystals contain regularly repeating regions of high and low n. A band gap that forbids propagation of certain wavelengths, i.e. disallowed bands of wavelengths, is called a photonic "stop-band". A one-dimensional photonic crystal typically comprises periodically alternating layers having different n. In a two-dimensional photonic crystal, the periodic variation of n takes place along two directions, typically two orthogonal axes. In a three-dimensional photonic crystal, the periodic variation of n takes place along three directions, typically the three orthogonal axes.

Due to their ability to selectively reflect certain wavelengths, one-dimensional planar photonic crystals have been used in a wide variety of optical applications including, but not limited to, distributed Bragg reflectors (DBR), also referred to as a Bragg stacks and optical filters. In general, the photonic crystals are constructed by sequentially forming dielectric layers with distinct compositions, typically magnesium fluoride, silicon dioxide, zinc sulfide, or titanium dioxide, to form the periodic structure of the photonic crystal. Accordingly, the number of layers required to achieve a desirable reflectivity can significantly affect manufacturing time and costs.

Currently, there is no infrared Bragg reflector that is entirely polymeric, particularly at the important IR wavelengths of 0.8-5 µm. This is mainly due to the fact that the refractive index of most polymers is very low, n~1.5-1.6. To date, organic plastics exhibit poor performance in the optical window of 1 to 10 µm due to strong IR absorption from the plastic materials, deriving largely from C—H bonds. Other systems based on "block copolymers" have been used to make a Bragg reflector, but are more difficult and expensive since these systems require precise manufacturing to achieve appropriate thin film morphologies. Furthermore, these systems are typically in the visible to near-IR regime. For example, Edrington et al. teaches a styrene-ethylene(propylene) block copolymer having a reflective peak at around 500 nm (A. C. Edrington et al./ Polymer-Based Photonic Crystals. *Adv. Mater.* 2001, 13. No. 6, March 16). As taught in Gazzo et al., hyperbranched polyvinylsulfide polymers (HB-PVS) show near ultraviolet absorption inducing an increased refractive index in the visible-near infrared (Gazzo et al., High Refractive Index Hyperbranched Polyvinylsulfides for Planar One-Dimensional All-Polymer Photonic Crystals. Journal of Polymer Science, Part B: Polymer Physics 2016, 54.73-80). As another example, Sveinbjörnsson et al. teaches brush block copolymers with photonic band gaps spanning the visible spectrum, from ultraviolet to near IR (Sveinbjörnsson et al., Rapid self-assembly of brush block copolymers to photonic crystals, www.pnas.org/cgi/doi/10.1073/pnas.1213055109). Polymers that exhibit ultra-high refractive index and high transparency in the visible and the IR can be utilized to prepare reflective coatings for the near IR (NIR) and the short wave IR (SWIR) which can be used for heat management for transparent windows in automobiles and housing.

Hence, there is a need for cheaper and more easily processable materials for optical mirrors and reflectors particularly in the short-wave infrared (SWIR) and mid-wave IR (MWIR) spectrum. Furthermore, the potential for making flexible optical mirrors and reflectors in the SWIR and MWIR would be advantageous in defense-related applications, where inorganic semiconductors (e.g., Ge, Si) and chalcogenide glasses have been widely used as materials for device components due to their high refractive index (n~2.0-4.0) and low losses from 1-10 µm. While such materials are well suited for these applications, they are inherently more expensive, toxic, and difficult to process in comparison to organic or organic/inorganic hybrid polymeric materials. High refractive index polymers (HRIPs) are a solution to this limitation, but to date, there are no reports of synthetic polymers that have sufficiently high n and that are IR transparent to enable this application.

While sulfur feedstocks are plentiful, sulfur is inherently difficult to process into films and molded objects, and previous synthetic methods have limited abilities to incorporate sulfur and create polymers with a high content of S—S bonds. In its original form, elemental sulfur consists of a cyclic molecule having the chemical formulation $S_8$. Elemental sulfur is a brittle, intractable, crystalline solid having poor solid state mechanical properties and poor solution processing characteristics. The inventors have previously developed a facile, one-step polymerization termed "inverse vulcanization" to prepare sulfur polymers from elemental sulfur. These sulfur polymers have a high content of S—S bonds in the polymer backbone ranging from 50-90 wt % sulfur that exhibited both high refractive index (n=1.9 to 1.7 from 600-1500 nm) and high IR transparency, in which further details can be found in co-owned U.S. Pat. Nos. 9,567,439 and 9,306,218, the specifications of which are incorporated herein in their entirety by reference.

As used herein, the chalcogenide hybrid inorganic/organic polymers (CHIPs) of the present invention are hybrids of sulfur, chalcogenides, and organic comonomers, and can have an ultra-high refractive index (n>1.7-2.2). These polymers utilize selenium to provide for improved optical properties. The polymerization of liquid $S_8$ with elemental selenium ($Se_8$) and/or cyclic selenium sulfides to form the chalcogenic sulfur polymer greatly increases the refractive index of said polymers. Further still, the CHIPs are solution processable, thereby making it easier and cheaper to fabricate Bragg reflectors, as compared to melt extrusion and high vacuum vapor deposition.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed

SUMMARY OF THE INVENTION

The inventors discovered certain polymeric materials, precursors thereof as well of methods of preparation thereof.

One aspect of the invention pertains to monomers for synthesizing high refractive index optical polymers, said monomer comprising the following structure:

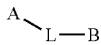

wherein A is a vinylic group, L is a functional linker, and B is a protecting group capable of being cleaved upon application of an external stimulus. The monomers of the invention may use to prepare polymer precursors for synthesizing high refractive index optical polymers, wherein said polymer precursor id prepared from polymerizing a plurality of these monomers.

The present invention has the unique and inventive technical features of a high refractive index range and an ability to change a refractive index of the polymer upon appropriate external stimuli during the process of polymerization. Without wishing to limit the invention to any theory or mechanism, it is believed that these technical features (i.e., stimuli responsiveness and large $\Delta n$) advantageously provide an attractive and low cost alternative that can meet a demand for optical devices that require variable and high refractive index materials. For example, the present invention allows for facile fabrication of polymer waveguide devices for use as optical interconnects (i.e., coupling two discrete optical elements or devices). None of the presently known prior references or work has the unique inventive technical feature of the present invention.

Another aspect of the invention pertains to chalcogenic hybrid inorganic/organic polymer (CHIP) composites, and the preparation thereof. For example, the present invention includes a chalcogenic hybrid inorganic/organic polymer (CHIP) composite comprising:
  a. about 5-99 wt % of a CHIP polymer matrix comprising:
    i. one or more sulfur monomers derived from elemental sulfur, at a level of at least 35 wt % of the CHIP polymer matrix;
    ii. elemental selenium ($Se_8$) at a level of at least 35 wt % of the CHIP polymer matrix; and
    iii. one or more comonomers each selected from a group consisting of amine comonomers, thiol comonomers, sulfide comonomers, alkynylly unsaturated comonomers, epoxide comonomers, nitrone comonomers, aldehyde comonomers, ketone comonomers, thiirane comonomers, ethylenically unsaturated comonomers, styrenic comonomers, vinylic comonomers, methacrylate comonomers, acrylonitrile comonomers, allylic monomers, acrylate monomers, vinylpyridine monomers, isobutylene monomers, maleimide monomers, norbornene monomers, monomers having at least one vinyl ether moiety, and monomers having at least one isopropenyl moiety, at a level in the range of about 5-50 wt % of the CHIP polymer matrix; and
  b. about 1-95 wt % variable loading of at least one isorefractive filler blended into the CHIP polymer matrix;
wherein the isorefractive filler has a refractive index (n) similar or identical to that of the CHIP polymer matrix over a range from n=1.3 to 2.7, and wherein the isorefractive filler is effective for reinforcing a thermomechanical property of the CHIP composite.

Furthermore, the CHIPs composite material may have the ability to self-heal upon reprocessing. Without wishing to limit the present invention to any particular theory or mechanism, it is believed that the self-healing property of these polymers are due to their reversible S—S bonds, which allows for broken S—S bonds to be reconnected by methods such as heat processing. Any optical substrate constructed from these CHIPs composite material may be reprocessable and repairable.

A further aspect of the present invention is directed to compositions and methods of fabricating optical mirrors and reflectors from chalcogenic hybrid inorganic/organic polymers (CHIPs).

The unique and inventive technical features of the present invention include the optical properties, such as high refractive index (RI) and high infrared transparency, and solution processability of the CHIPs. Without wishing to limit the invention to any theory or mechanism, it is believed that these technical features advantageously allow for facile processing of these materials with other inexpensive, commercially available low RI polymers to produce optical devices for use in infrared applications. None of the presently known prior references or work has the unique inventive technical feature of the present invention.

In one embodiment, the optical devices are made by spin-coating polymer films with alternating layers of CHIPs and a low-refractive index polymer, such as cellulose acetate or poly(vinyl alcohol). Preferably, the CHIPs and the low RI polymers are dissolved in differing solvents that do not affect the underlying polymer film layer. By varying and tuning the film thickness and number of layers of the polymer films, as well as the composition of the polymer solutions, optical mirrors and reflectors may be fabricated for use in a wide range of IR applications, e.g. SWIR and mid-IR.

BRIEF DESCRIPTION OF THE DRAWINGS

The features and advantages of the present invention will become apparent from a consideration of the following detailed description presented in connection with the accompanying drawings in which.

Figure 1:
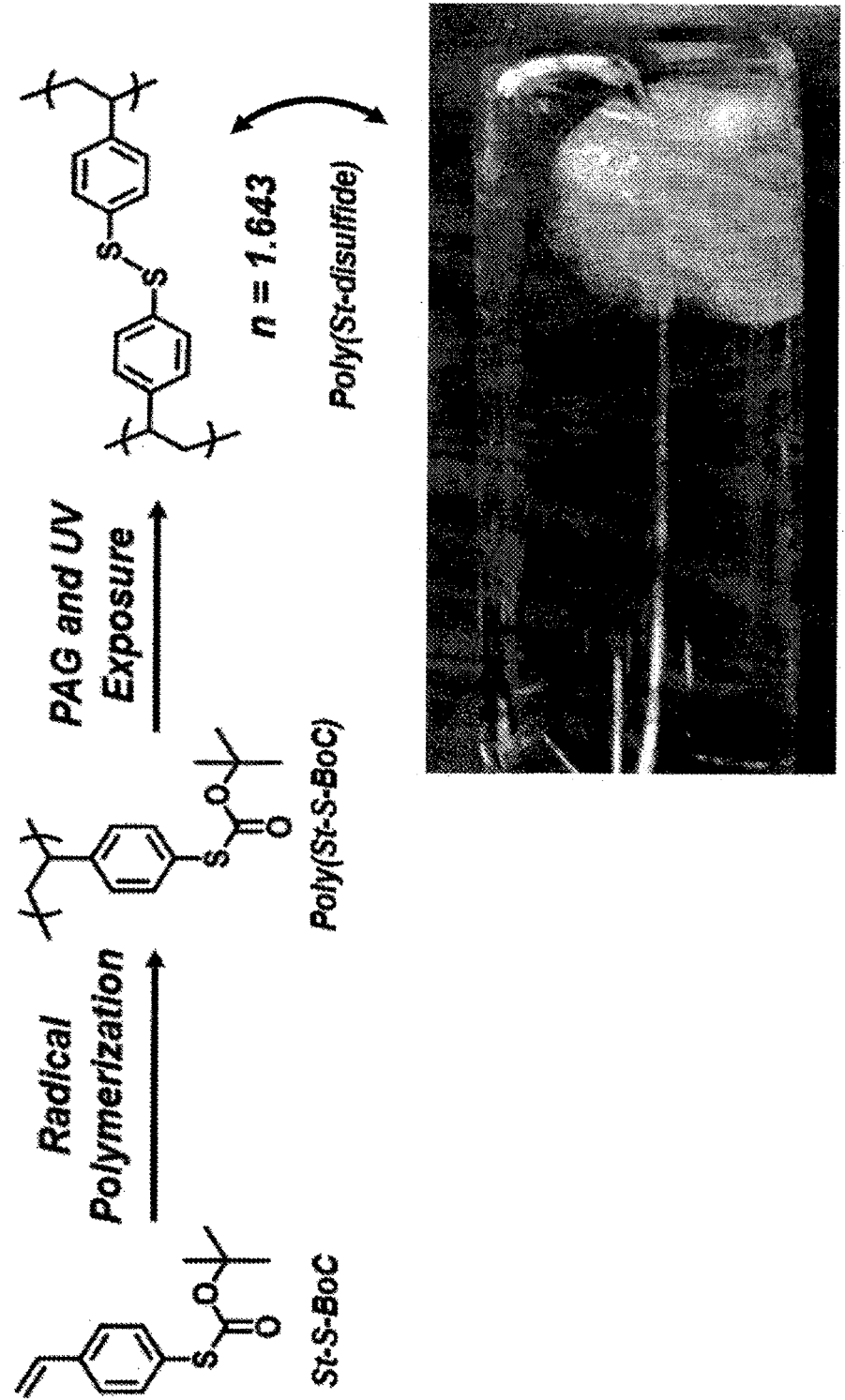
FIG. 1 shows an exemplary embodiment where the novel organic compound, O-tert-butyl-S-(vinylphenyl)carbonothioate (St-S-BOC), undergoes radical polymerization to produce a polymer, poly(St-S-BOC). Poly(St-S-BOC) is further deprotected to produce an optical polymer, poly(St-disulfide), having a high refractive index.
Figure 2:
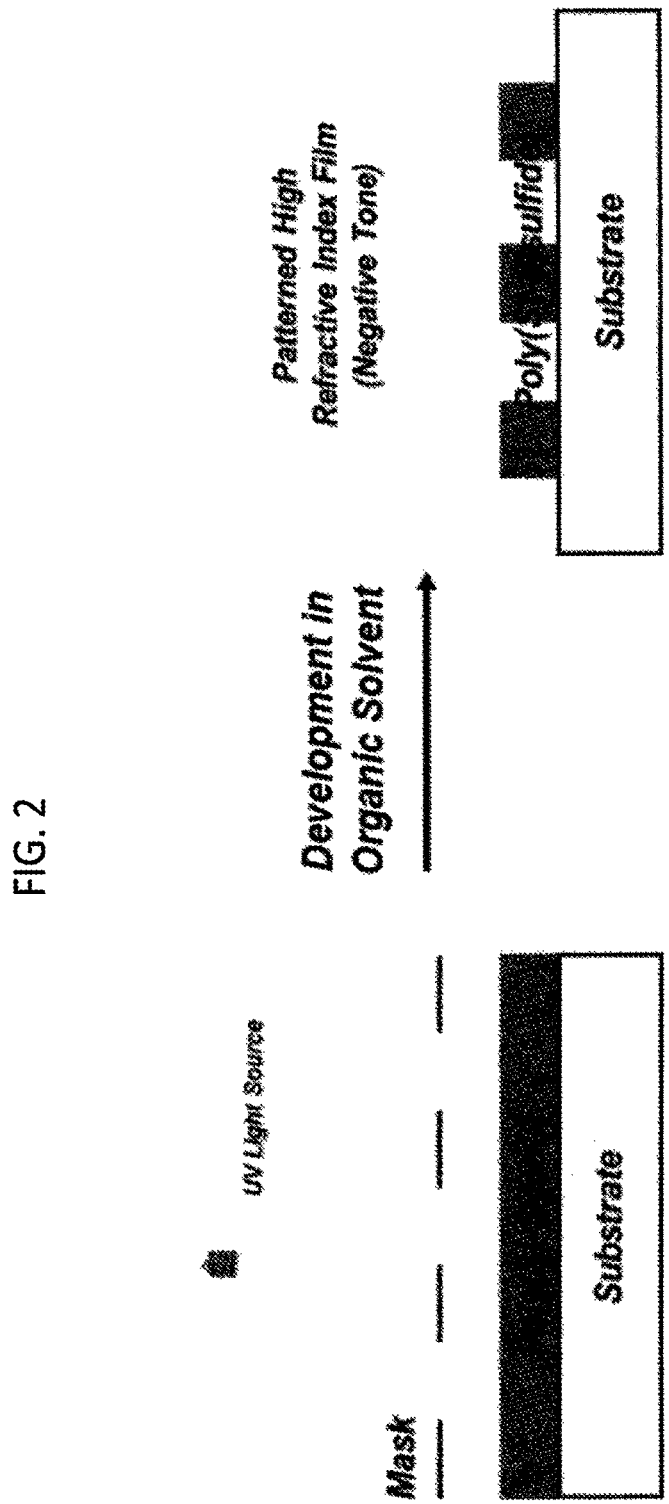
FIG. 2 shows an exemplary embodiment of developing poly(St-S-BOC) to form a patterned film of the high refractive index optical polymer, poly(St-disulfide).
Figure 3:
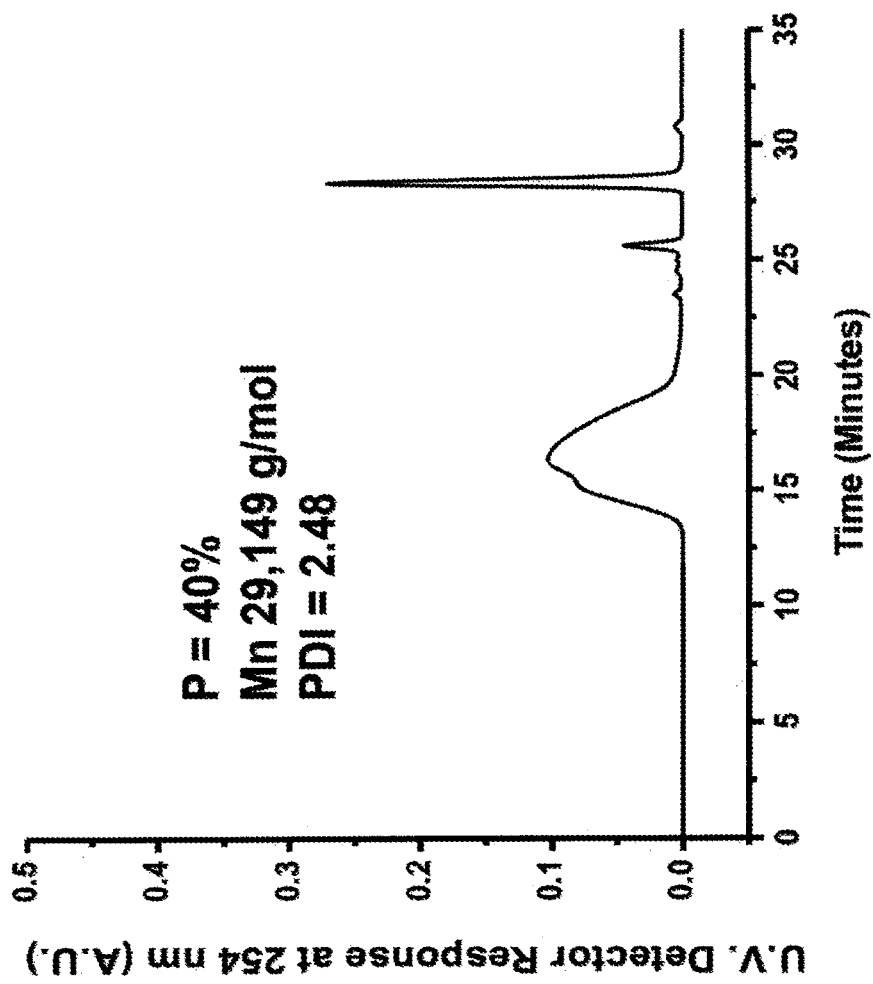
FIG. 3 shows a size exclusion chromatogram of poly(Sty-SBOC).

DETAILED DESCRIPTION 1.0. Photorefractive, High Refractive Optical Polymers from Styrenic Sulfide Monomers The present invention features the creation of a new monomer and polymer precursor that has irreversible change in refractive index upon exposure to external stimuli, such as light (i.e., a photochemically tunable polymer). Some polymers have been reported to exhibit photorefractive properties; however, these optical changes are often reversible, for example, photoisomerization of azobenzene containing polymers, and hence, are not useful in certain optical device applications. In one embodiment of the invention, the present photorefractive polymers carries a BOC protecting group that can be deprotected using UV irradiation in the presence of a photoacid generator (PAG), in an irreversible fashion. This class of photoresponsive polymers has a large change in refractive index between the t-BOC protected polymer (n=1.55) and the UV deprotected polymer (n=1.65), which is a change in refractive index of $\Delta n=0.1$. This is significantly larger than the state of the art, which typically uses a $\Delta n \geq 0.01$. These novel monomer and polymer precursors are well suited for the fabrication of integrated photonics devices, waveguides, Bragg gratings, phase masks, polymer interconnects, and other optical devices.

In one preferred embodiment, the present invention features an innovative styrenic sulfide monomer, O-tert-butyl-S-(vinylphenyl)carbonothioate (Sty-S-BOC), where the thiol group is protected with a tert-butyloxycarbonyl (BOC) protecting group. As shown in Scheme 1, the styrenic sulfide monomer can be free radically polymerized using conventional free radical initiators, such as thermal initiation using azo or peroxide initiators, or photoinitiation, or controlled radical polymerizations, such as RAFT, ATRP, or nitroxide mediated polymerizations (NMP). In another preferred embodiment, the polymer precursor from this monomer (Sty-S-BOC) can be solution, or melt processed into films, or other free standing forms that can be readily treated via thermal, light, or chemical methods. Without wishing to limit the invention to a particular theory or mechanism, these eternal stimuli can deprotect the t-BOC protecting group to unmask the free thiol group to prepare poly(4-vinylbenzenethiol), which forms disulfide bonds (S—S) spontaneously in air, thereby producing crosslinked (poly(Sty-S—S) polymers. This chemical deprotection process is accompanied by a sharp increase in refractive index and the formation of crosslinked, thermoset optical polymeric materials having high refractive indexes.

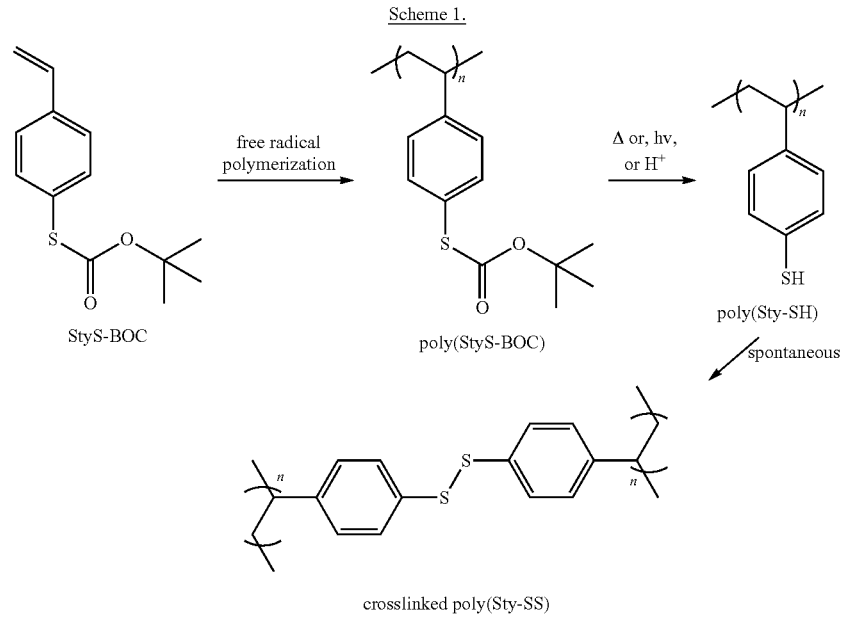

Scheme 1.

According to some embodiments, the present invention features a monomer for synthesizing high refractive index optical polymers, said monomer comprising the following structure:

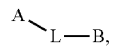

where A is a vinylic group. L is a functional linker, and B is a protecting group capable of being cleaved upon application of an external stimuli.

In one embodiment, a polymer precursor for synthesizing high refractive index optical polymers may be prepared by polymerizing the monomers. For instance, the vinylic group of each monomer undergoes a radical polymerization to produce the polymer precursor. In another embodiment, an optical polymer having a high refractive index can be prepared from the polymer precursor. Without wishing to limit the invention to a particular theory or mechanism, the polymer precursor can be deprotected to remove the protecting group, thereby resulting in an irreversible change in refractive index, Δn, and producing the optical polymer, wherein Δn is greater than about 0.01. In some embodiments, the high refractive index of the optical polymer may be at least about 1.6. In other embodiments. An can range from about 0.01 to about 0.1.

In some embodiments, the vinylic group, A, may be a divinylic, multivinylic, or polyunsaturated group. Examples of the vinylic group, A, include, but are not limited to, styrenics, acrylates, methacrylates, acrylamides, methacrylamides, or divinylbenzenes. In other embodiments, the functional linker, L, may be a sulfide moiety, a selenium (Se) moiety, a tin (Sn) moiety, a titanium (Ti) moiety, a tellurium (Te) moiety, an aromatic or heteroaromatic moiety having a high molar refractive index, an aliphatic moiety, or an unsaturated moiety. In still other embodiments, the protecting group, B, may be a tert-butyloxycarbonyl (BOC), t-butyl esters, or nitrobenzyl ethers. In preferred embodiments, the protecting group, B, can be cleavable by application of an acid, a photoacid generator, heat, light irradiation, or a combination thereof.

In one embodiment, the polymer precursor can be deprotected by application of an acid, a photoacid generator, heat, light irradiation, or a combination thereof. The deprotected functional linker of the polymer precursor can then covalently bind to a deprotected functional linker of another polymer precursor, thereby forming the optical polymer.

According to another embodiment of the present invention, the monomer (St-SBOC) for synthesizing high refractive index optical polymers may comprise the following structure:

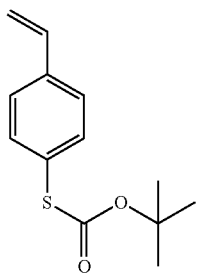 [SMILES: C=Cc1ccc(SC(=O)OC(C)(C)C)cc1]

In one embodiment, a polymer precursor (poly(St-SBOC)) for synthesizing high refractive index optical polymers may be prepared by polymerizing the St-SBOC monomers. For example, the styrenic group of each monomer undergoes a radical polymerization to produce the poly(St-SBOC) according to the following structure:

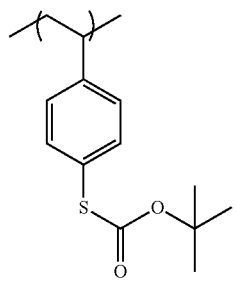

In another embodiment, an optical polymer (poly(St-disulfide)) having a high refractive index may be prepared from the poly(St-SBOC) precursor. The polymer precursor is deprotected to remove the tert-butyloxycarbonyl group via an acid, a photoacid generator, heat, light irradiation, or a combination thereof. The deprotected sulfide of the polymer precursor covalently binds to a deprotected sulfide of another polymer precursor, thereby producing the poly(St-disulfide) optical polymer according to the following structure:

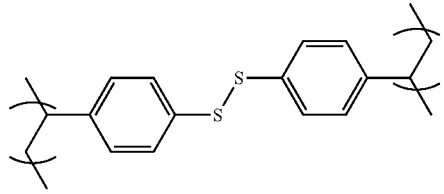

Further still, the deprotection can result in an irreversible change in refractive index, Δn, which is preferably greater than about 0.01. For example, Δn can range from about 0.01 to about 0.1. In more preferred embodiments, the high refractive index of the optical polymer is at least about 1.6.

According to yet another embodiment, the present invention features an optical device comprising any of the optical polymers described herein. Examples of the optical device include, but are not limited to photonics devices such as an optical waveguide, a Bragg grating, a phase mask, a waveguide grating router, a polymer interconnect, an echelle grating, a directional coupler and a Mach-Zehnder interferometer.

According to other embodiments, the present invention features a method of preparing an optical device having a high refractive index. In one embodiment, the method may comprise providing a substrate, applying any of the polymer precursors described herein to a surface of the substrate, applying an external stimulus to the polymer precursor applied to the substrate such that the polymer precursor undergoes a deprotection to remove the protecting group, thereby resulting in an irreversible change in refractive index, Δn, and producing the optical device, in preferred embodiments, the high refractive index of the optical device may be at least about 1.6. In other preferred embodiments, Δn can greater than about 0.01. For instance, Δn can range from about 0.01 to about 0.1.

In some embodiments, the polymer precursor may be applied using spin-coating techniques to produce a thin film of the polymer precursor. In other embodiments, the external stimulus is an acid, a photoacid generator, heat, light irradiation, or a combination thereof. In still other embodiments, the method may further comprise performing a photolithographic technique to pattern a film of the polymer precursor by removing the protecting group of the polymer precursor, thereby increasing the refractive index and producing a patterned optical device.

In yet other embodiments, the present invention features a method of producing a monomer according to the following structure:

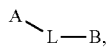

wherein A is a vinylic group, L is a functional linker, and B is a protecting group. In one embodiment, the method may comprise reacting a vinylic compound comprising the vinylic group A with a high refractive index compound to form a high refractive index vinylic compound having the functional linker L, and reacting the high refractive index vinylic compound with a protecting compound having the protecting group B, where the protecting group B covalently binds to the functional linker L, thereby producing the monomer.

In some embodiments, the reaction of the vinylic compound with the sulfur compound may be performed at a temperature of about −80° C. to −50° C. In other embodiments, the reaction of the vinylic sulfide compound with the protecting compound may be performed at a temperature of about −30° C. to −10° C.

In some embodiments, the vinylic group A may be a divinylic, multivinylic, or polyunsaturated group. In other embodiments, the vinylic group A may be a styrenic, an acrylate, a methacrylate, an acrylamide, a methacrylamide, or a divinylbenzene. In still other embodiments, the vinylic compound may further comprise a leaving group, such as a halide, which is replaced by the functional linker L.

In preferred embodiments, the high refractive index compound may be a chalcogenide, elemental sulfur, sulfur compound, selenium compound, tin compound, titanium compound, a tellurium compound, or any other compound having moieties of high molar refraction. In other embodiments, the functional linker L may be a sulfide moiety, Se moiety, Sn moiety, Ti moiety, Te moiety an aromatic or heteroaromatic moiety having a high molar refractive index, an aliphatic moiety, or an unsaturated moiety. Without wishing to limit the invention to a particular theory or mechanism, the high refractive index compound, namely the functional linker substituent, can be effective to increase a refractive index of the vinylic compound.

In one embodiment, the protecting group B may be a tert-butyloxycarbonyl (BOC), t-butyl ester, or nitrobenzyl ether. Preferably, the protecting group B can be cleavable upon application of an external stimulus, such as, for example, an acid, a photoacid generator, heat, light irradiation, or a combination thereof.

In some embodiments, the invention encompasses a monomer for synthesizing high refractive index optical polymers, said monomer comprising the following structure:

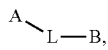

wherein A is a vinylic group, L is a functional linker, and B is a protecting group capable of being cleaved upon application of an external stimulus.

In further embodiments, the present invention is a monomer, wherein the vinylic group A, is a divinylic, multivinylic, or polyunsaturated group.

In some embodiments, the present invention is a monomer, wherein the vinylic group, A, is a styrenic, an acrylate, a methacrylate, an acrylamide, a methacrylamide, or a divinylbenzene.

In some embodiments, the present invention is a monomer, wherein the functional linker, L, is a sulphide moiety, an aromatic or heteroaromatic moiety having a high molar refractive index, an aliphatic moiety, or an unsaturated moiety.

In some embodiments, the present invention is a monomer, wherein the protecting group, B, is a tert-butyloxycarbonyl (BOC), t-butyl esters, or nitrobenzyl ethers.

In some embodiments, the present invention is a monomer, wherein the protecting group, B, is cleaveable by application of an acid, a photoacid generator, heat, light irradiation, or a combination thereof.

In some embodiments, the present invention encompasses a polymer precursor for synthesizing high refractive index optical polymers, said polymer precursor prepared from polymerizing a plurality of monomers according to the invention. In further embodiments, the polymer precursor of the invention, wherein the vinylic group of each monomer may undergoes a radical polymerization to produce the polymer precursor.

In some embodiments, the present invention encompasses an optical polymer having a high refractive index, said optical polymer prepared from a polymer precursor of the invention, wherein the polymer precursor is deprotected to remove the protecting group, thereby resulting in an irreversible change in refractive index, Δn, and producing an optical polymer, wherein Δn is greater than about 0.01. In some embodiments, the high refractive index of the optical polymer is at least about 1.6. In further embodiments, Δn ranges from about 0.01 to about 0.1.

In some embodiments, the invention encompasses an optical polymer wherein the polymer precursor is deprotected by application of an acid, a photoacid generator, heat, light irradiation, or a combination thereof. In further embodiments, the invention encompasses an optical polymer, wherein the deprotected functional linker of the polymer precursor covalently binds to a deprotected functional linker of another polymer precursor, thereby forming the optical polymer.

In some embodiments, the invention encompasses a monomer (Sty-SBOC) for synthesizing high refractive index optical polymers, said monomer comprising the following structure:

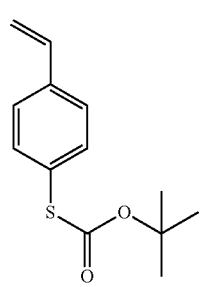 [SMILES: C=Cc1ccc(SC(=O)OC(C)(C)C)cc1]

In some embodiments, the invention encompasses a polymer precursor for synthesizing high refractive index optical polymers, said polymer precursor prepared from polymerizing a plurality of monomers according to the invention.

In some embodiments, the invention encompasses a polymer precursor, wherein the styrenic group of each monomer undergoes a radical polymerization to produce the polymer precursor according to the following structure:

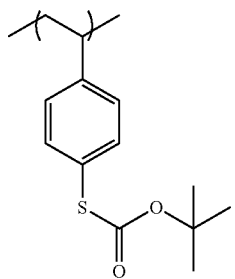

In some embodiments, the invention encompasses an optical polymer having a high refractive index, wherein said optical polymer is prepared from a polymer precursor according to the invention, wherein the polymer precursor is deprotected to remove the tert-butyloxycarbonyl group, thereby resulting in an irreversible change in refractive index, Δn, greater than about 0.01, and producing the optical polymer according to the following structure:

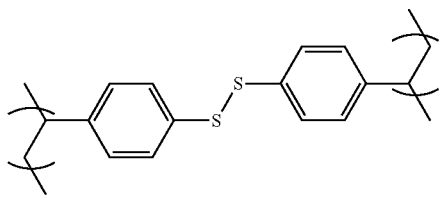

In further embodiments, the present invention is an optical polymer, wherein the high refractive index of the optical polymer is at least about 1.6. In further embodiments, wherein Δn ranges from about 0.01 to about 0.1.

In further embodiments, the present invention is an optical polymer, wherein the polymer precursor thereof is deprotected by application of an acid, a photoacid generator, heat, light irradiation, or a combination thereof. In some embodiments, the deprotected sulfide of the polymer precursor covalently binds to a deprotected sulfide of another polymer precursor, thereby forming the optical polymer.

Another further aspect of the invention is an optical device comprising an optical polymer as disclosed herein. In some embodiments, the optical device is a photonics device such as an optical waveguide, a Bragg grating, a phase mask, a waveguide grating router, a polymer interconnect, an echelle grating, a directional coupler and a Mach-Zehnder interferometer.

A further aspect of the invention is a method of preparing an optical device having a high refractive index, said method comprising:
  providing a substrate;
  applying a polymer precursor of the present invention to a surface of the substrate:
  applying an external stimulus to the polymer precursor applied to the substrate, wherein the polymer precursor undergoes a deprotection to remove the protecting group, thereby resulting in an irreversible change in refractive index, Δn, and producing the optical device, wherein Δn is greater than about 0.01.

In some embodiments, the method of preparing an optical device having a high refractive index involves the high refractive index of the optical device is at least about 1.6. In further embodiments, the method of preparing an optical device having a high refractive index involves a Δn ranging from about 0.01 to about 0.1. In further embodiments, the method may include applying the polymer precursor using spin-coating techniques to produce a thin film of the polymer precursor. In some embodiments, the method includes an external stimulus, wherein the external stimulus is an acid, a photoacid generator, heat, light irradiation, or a combination thereof.

In some embodiments of the invention, the method of preparing an optical device having a high refractive index further comprises performing a photolithographic technique to pattern a film of the polymer precursor by removing the protecting group of the polymer precursor, thereby increasing the refractive index. In further embodiments, the method includes a photolithographic technique, wherein the photolithographic technique produces a patterned optical device.

A further aspect of the invention pertains to a method of producing a monomer according to the following structure:

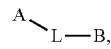

wherein A is a vinylic group, L is a functional linker, and B is a protecting group, wherein said method comprises:
  reacting a vinylic compound comprising the vinylic group A with a high refractive index compound to form a high refractive index vinylic compound having the functional linker L; and
  reacting the high refractive index vinylic compound with a protecting compound having the protecting group B, wherein the protecting group B covalently binds to the functional linker L, thereby producing the monomer;
  wherein the protecting group B is capable of being cleaved upon application of an external stimulus.

In some embodiments, the method includes a monomer, wherein the vinylic group A is a divinylic, multivinylic, or polyunsaturated group.

In some embodiments, the method includes a monomer, wherein the vinylic group A is a styrenic, an acrylate, a methacrylate, an acrylamide, a methacrylamide, or a divinylbenzene.

In some embodiments, the method includes a vinylic compound, wherein vinylic compound further comprises a leaving group, wherein the leaving group is replaced by the functional linker L.

In some embodiments, the method of producing a monomer according to A-L-B involves use of a leaving group, wherein the leaving group is a halide. In further embodiments, this method may involve a high refractive index compound, wherein the high refractive index compound is a chalcogenide, elemental sulfur, sulfur compound, selenium compound, tin compound, titanium compound, or any other compound having moieties of high molar refraction. In other embodiments, the high refractive index compound is effective to increase a refractive index of the vinylic compound. In further embodiments, the functional linker L is a sulfide moiety, Se moiety, Sn moiety, Ti moiety, an aromatic or heteroaromatic moiety having a high molar refractive index, an aliphatic moiety, or an unsaturated moiety. In some embodiments, the protecting group B is a tert-butyloxycarbonyl (BOC), t-butyl ester, or nitrobenzyl ether. In further embodiments, the protecting group B is cleavable by application of an acid, a photoacid generator, heat, light irradiation, or a combination thereof. In further embodiments, the method involves reaction of the vinylic compound with the sulfur compound, wherein the reaction of the vinylic compound with the sulfur compound is performed at a temperature of about −80° C. to −50° C. Furthermore, the method may include reaction of the vinylic sulfide compound with the protecting compound, wherein the reaction of the vinylic sulfide compound with the protecting compound is performed at a temperature of about −30° C. to −10° C.

2.0. Reinforced Chalcogenide Hybrid Inorganic/Organic Polymers (CHIPs) Composites with Isorefractive Fillers

[158]

As used herein, sulfur can be provided as elemental sulfur, for example, in powdered form. Under ambient conditions, elemental sulfur primarily exists in an eight-membered ring form (S8) which melts at temperatures in the range of 120° C.-130° C. and undergoes an equilibrium ring-opening polymerization (ROP) of the S8 monomer into a linear polysulfane with diradical chain ends. As the person of skill in the art will appreciate, while S8 is generally the most stable, most accessible and cheapest feedstock, many other allotropes of sulfur can be used (such as other cyclic allotropes, derivable by melt-thermal processing of S8). Any sulfur species that yield diradical or anionic polymerizing species when heated as described herein can be used in practicing the present invention.

As used herein, "composite" generally refers to a heterophasic mixture of materials with a well-defined interface. For example, when particles are added to a CHIP, it becomes a polymer-particle composite, which is considered a "CHIP composite." The term "composite" is used interchangeably with "material" when referring to chalcogenic hybrid inorganic/organic polymer (CHIP) embodiments within the scope of the invention. Therefore, "CHIP material" may be used interchangeably with "CHIP composite" within the metes and bounds of the present invention.

As used herein, a "styrenic comonomer" is a monomer that has a vinyl functional group. The styrenic comonomer may comprise a styrene and at least one reactive functional group. As known to one of ordinary skill in the art, a styrene is a derivative of benzene ring that has a vinylic moiety. The sulfur diradicals can link to the vinylic moieties of the styrenic commoners to form the sulfur-styrenic polymer. In certain embodiments, the reactive functional group may be a halogen, an alkyl halide, an alkyl, an alkoxy, an amine, or a nitro functional group. Non-limiting examples of styrenic comonomers include bromostyrene, chlorostyrene, fluorostyrene, (trifluoromethyl)styrene, vinylaniline, acetoxystyrene, methoxystyrene, ethoxystyrene, methylstyrene, nitrostyrene, vinylbenzoic acid, vinylanisole, and vinylbenzyl chloride.

As used herein, the term "amine monomer" is a monomer that has an amine functional group. In one embodiment, aromatic amines and multi-functional amines may be used. Amine monomers include, but are not limited to, aromatic amines, m-phenylenediamine, and p-phenylenediamine. The various types of phenylenediamines are inexpensive reagents due to their wide-spread use in the preparation of many conventional polymers, e.g., polyureas, polyamides As used herein, the term "thiol monomer" is a monomer that has a thiol functional group. Thiol monomers include, but are not limited to, 4,4'-thiobisbenzenethiol and the like. The term "sulfide monomers" are monomers that have sulfide functional groups.

As used herein, an alkynylly unsaturated monomer is a monomer that has an alkynylly unsaturated functional group (i.e. triple bond). The term "alkynylly unsaturated monomer" does not include compounds in which the alkynyl unsaturation is part of a long chain alkyl moiety (e.g., unsaturated fatty acids, or carboxylic salts, or esters such as oleates, and unsaturated plant oils). In one embodiment, aromatic alkynes, both internal and terminal alkynes, multifunctional alkynes may be used. Examples of alkynylly unsaturated monomers include, but are not limited to, ethynylbenzene, 1-phenylpropyne, 1,2-diphenylethyne, 1,4-diethynylbenzene, 1,4-bis(phenylethynyl) benzene, and 1,4-diphenylbuta-1,3-diyne.

As used herein, the term "nitrone monomer" is a monomer that has a nitrone groups. In one embodiment, nitrones, dinitrones, and multi-nitrones may be used. Examples include, but are not limited to, N-benzylidene-2-methylpropan-2-amine oxide.

As used herein, the term "aldehyde monomer" is a monomer that has an aldehyde functional group. In one embodiment, aldehydes, dialdehydes, and multi-aldehydes may be used.

As used herein, the term "ketone monomer" Is a monomer that has a ketone functional group. In one embodiment, ketones, di-ketones, and multi-ketones may be used.

As used herein, the term "epoxide monomer" is a monomer that has epoxide functional groups. Non-limiting examples of such monomers include, generally, mono- or polyoxiranylbenzenes, mono- or polyglycidylbenzenes, mono- or polyglycidyloxybenzenes, mono- or polyoxiranyl (hetero)aromatic compounds, mono- or polyglycidyl(hetero) aromatic compounds, mono- or polyglycidyloxy(hetero)aromatic compounds, diglycidyl bisphenol A ethers, mono- or polyglycidyl(cyclo)alkyl ethers, mono- or polyepoxy(cyclo) alkane compounds and oxirane-terminated oligomers. In one preferred embodiment, the epoxide monomers may be benzyl glycidyl ether and tris(4-hydroxyphenyl)methane triglycidyl ether. In certain embodiments, the epoxide monomers may include a (hetero)aromatic moiety such as, for example, a phenyl, a pyridine, a triazine, a pyrene, a naphthalene, or a polycyclic (hetero)aromatic ring system, bearing one or more epoxide groups. For example, in certain embodiments, the one or more epoxide monomers are selected from epoxy(hetero)aromatic compounds, such as styrene oxide and stilbene oxide and (hetero)aromatic glycidyl compounds, such as glycidyl phenyl ethers (e.g., resorcinol diglycidyl ether, glycidyl 2-methylphenyl ether), glycidylbenzenes (e.g., (2,3-epoxypropyl)benzene) and glycidyl heteroaromatic compounds (e.g., N-(2,3-epoxypropyl)phthalimide). In certain desirable embodiments, an epoxide monomer will have a boiling point greater than 180° C., greater than 200° C., or even greater than 230° C. at the pressure at which polymerization is performed (e.g., at standard pressure, or at other pressures).

As used herein, the term "thiirane monomer" is a monomer that has a thirane functional group. Non-limiting examples of thiirane monomers include, generally, mono- or polythiiranylbenzenes, mono- or polythiiranylmethylbenzenes, mono- or polythiiranyl(hetero)aromatic compounds, mono- or polythiiranylmethyl(hetero)-aromatic compounds, dithiiranylmethyl bisphenol A ethers, mono- or polydithiiranyl (cyclo)alkyl ethers, mono- or polyepisulfide(cyclo) alkane compounds, and thiirane-terminated oligomers. In some embodiments, thiirane monomers may include a (hetero)aromatic moiety such as, for example, a phenyl, a pyridine, a triazine, a pyrene, a naphthalene, or a poly cyclic (hetero)aromatic ring system, bearing one or more thiirane groups. In certain desirable embodiments, a thiirane monomer can have a boiling point greater than 180° C., greater than 200° C., or even greater than 230° C. at the pressure at which polymerization is performed (e.g., at standard pressure).

As used herein, an ethylenically unsaturated monomer is a monomer that contains an ethylenically unsaturated functional group (i.e. double bond). The term "ethylenically unsaturated monomer" does not include cyclopentadienyl species such as cyclopentadiene and dicyclopentadiene. The term "ethylenically unsaturated monomer" does not include compounds in which the ethylenic unsaturation is part of a long chain alkyl moiety (e.g. unsaturated fatty acids such as oleates, and unsaturated plant oils).

Non-limiting examples of ethylenically unsaturated monomers include vinyl monomers, acryl monomers, (meth)acryl monomers, unsaturated hydrocarbon monomers, and ethylenically-terminated oligomers. Examples of such monomers include, generally, mono- or polyvinylbenzenes, mono- or polyisopropenylbenzenes, mono- or polyvinyl(hetero)aromatic compounds, mono- or polyisopropenyl(hetero)-aromatic compounds, acrylates, methacrylates, alkylene di(meth)acrylates, bisphenol A di(meth)acrylates, benzyl (meth)acrylates, phenyl(meth)acrylates, heteroaryl (meth)acrylales, terpenes (e.g., squalene) and carotene. In other embodiments, the ethylenically unsaturated monomers may include a (hetero)aromatic moiety such as, for example, phenyl, pyridine, triazine, pyrene, naphthalene, or a polycyclic (hetero)aromatic ring system, bearing one or more vinylic, acrylic or methacrylic substituents. Examples of such monomers include benzyl (meth)acrylates, phenyl (meth)acrylates, divinylbenzenes (e.g., 1,3-divinylbenzene, 1,4-divinylbenzene), isopropenylbenzene, styrenics (e.g., styrene, 4-methylstyrene, 4-chlorostyrene, 2,6-dichlorostyrene, 4-vinylbenzyl chloride), diisopropenylbenzenes (e.g., 1,3-diisopropenylbenzene), vinylpyridines (e.g., 2-vinylpyridine, 4-vinylpyridine), 2,4,6-tris((4-vinylbenzyl) thio)-1,3,5-triazine and divinylpyridines (e.g., 2,5-divinylpyridine). In certain embodiments, the ethylenically unsaturated monomers (e.g., including an aromatic moiety) bear an amino (i.e., primary or secondary) group, a phosphine group or a thiol group. One example of such a monomer is vinyldiphenylphosphine. In certain desirable embodiments, an ethylenically unsaturated monomer will have a boiling point greater than 180° C. greater than 200° C., or even greater than 230° C. at the pressure at which polymerization is performed (e.g., at standard pressure).

As used herein, the term "self-healing" is defined as to enable a material to repair damage with minimum intervention. In some embodiments, mechanisms and techniques to enable self-healing may include covalent bonding, supramolecular chemistry, H-bonding, ionic interactions, π-π stacking, chemo-mechanical repairs focusing on encapsulation, remote self-healing, or shape memory assisted polymers. In one preferred embodiment, self-healing utilizes thermal reformation. As used herein, thermal reformation involves the use of heat to reform the bonds or cross-links of a polymeric material.

As used herein, the term "functional" in correlation with a polymer refers to functional polymers that have specified physical, chemical, biological, pharmacological, or other properties or uses that are determined by the presence of specific chemical functional groups, which are usually dissimilar to those of the backbone chain of the polymer.

As used herein, the term "chalcogenide" refers to a compound containing one or more chalcogen elements. One of ordinary skill in the art will understand that the classical chalcogen elements are sulfur, selenium and tellurium. In accordance with the present invention, the use of chalcogenide refers to compounds and/or polymers containing selenium.

As known to one of ordinary skill in the art, the term "isomer" refers to compounds having the same formula but differ in arrangement. For instance, isomers of cyclic selenium sulfides, such as $Se_2S_6$ and $Se_3S_5$, can have different placements of the Se units in the ring (e.g., S—Se—Se—S or S—S—S). Isomers of $Se_2S_6$ include 1,2-isomers, 1,3-isomers, 1,4-isomers, and 1,5-isomers, wherein the numbers refer to the position of the Se units in the eight-membered ring.

As known to one of ordinary skill in the art, the term "visible" refers to a portion of the electromagnetic spectrum that falls in the range of 390 to 700 nm. As used herein, the term "infrared" (IR) refers to a portion of the electromagnetic spectrum that falls in the range of 700 nm to 1 mm. Subsets of the IR spectrum include near-IR (700 nm to 3 μm), mid-IR (3-8 μm), long-wavelength IR (8-15 μm) and far-IR (15 μm to 1 mm).

As used herein, the terms "those defined above" and "those defined herein" when referring to a variable incorporates by reference the broad definition of the variable as well as any narrow and/or preferred, more preferred and most preferred definitions, if any.

According to one embodiment, the present invention features a chalcogenic hybrid inorganic/organic polymer (CHIP) composite comprising about 5-99 wt % of a CHIP polymer matrix and about 1-95 wt % variable loading of at least one isorefractive filler blended into the CHIP polymer matrix. Preferably, the isorefractive filler has a refractive index (n) similar or identical to that of the CHIP polymer matrix over a range from n=1.3 to 2.7. Without wishing to limit the invention to a particular theory or mechanism, the isorefractive filler can be effective for reinforcing a thermomechanical property of the CHIP composite.

In some embodiments, the CHIP polymer matrix may comprise one or more sulfur monomers derived from elemental sulfur at a level of at least 35 wt % of the CHIP polymer matrix, elemental selenium ($Se_8$) at a level of at least 35 wt % of the CHIP polymer matrix, and one or more comonomers each selected from a group consisting of amine comonomers, thiol comonomers, sulfide comonomers, alkynylly unsaturated comonomers, epoxide comonomers, nitrone comonomers, aldehyde comonomers, ketone comonomers, thiirane comonomers, ethylenically unsaturated comonomers, styrenic comonomers, vinylic comonomers, methacrylate comonomers, acrylonitrile comonomers, allylic monomers, acrylate monomers, vinylpyridine monomers, isobutylene monomers, maleimide monomers, norbornene monomers, monomers having at least one vinyl ether moiety, and monomers having at least one isopropenyl moiety, at a level in the range of about 5-50 wt % of the CHIP polymer matrix.

In one embodiment, for example, the CHIP polymer matrix may comprise at least about 50 wt % of the sulfur monomers. In another embodiment, the CHIP polymer matrix may comprise at least about 50 wt % of $Se_8$. In a further embodiment, the CHIP polymer matrix may comprise about 35-50 wt % of sulfur monomers, about 35-50 wt % of elemental selenium, and about 15-25 wt % of the comonomers.

In other embodiments, the CHIP polymer matrix may comprise one or more chalcogenic monomers at a level of at least 35 wt % of the CHIP polymer matrix, and one or more comonomers each selected from a group consisting of amine comonomers, thiol comonomers, sulfide comonomers, alkynylly unsaturated comonomers, epoxide comonomers, nitrone comonomers, aldehyde comonomers, ketone comonomers, thiirane comonomers, ethylenically unsaturated comonomers, styrenic comonomers, vinylic comonomers, methacrylate comonomers, acrylonitrile comonomers, allylic monomers, acrylate monomers, vinylpyridine monomers, isobutylene monomers, maleimide monomers, norbornene monomers, monomers having at least one vinyl ether moiety, and monomers having at least one isopropenyl moiety, at a level in the range of about 5-50 wt % of the CHIP polymer matrix. In one embodiment, the chalcogenic monomers are may comprise elemental sulfur, a liquid polysulfide, a liquid chalcogenide polymer, an oligomer containing sulfur, an oligomer containing sulfur and selenium units, or a combination thereof.

In some embodiments, the CHIP polymer matrix may further comprise one or more termonomers selected from a group consisting of a vinyl monomer, an isopropenyl monomer, an acryl monomer, a methacryl monomer, an unsaturated hydrocarbon monomer, an epoxide monomer, a thiirane monomer, an alkynyl monomer, a diene monomer, a butadiene monomer, an isoprene monomer, a norbornene monomer, an amine monomer, a thiol monomer, a sulfide monomer, an alkynylly unsaturated monomer, a nitrone monomer, an aldehyde monomer, a ketone monomer, an ethylenically unsaturated monomer, and a styrenic monomer.

In other embodiments, the CHIP polymer matrix may further comprise one or more polyfunctional monomers selected from a group consisting of a polyvinyl monomer, a polyisopropenyl monomer, a polyacryl monomer, a polymethacryl monomer, a polyunsaturated hydrocarbon monomer, a polyepoxide monomer, a polythiirane monomer, a polyalkynyl monomer, a polydiene monomer, a polybutadiene monomer, a polyisoprene monomer, a polynorbornene monomer, a polyamine monomer, a polythiol monomer, a polysulfide monomer, a polyalkynylly unsaturated monomer, a polynitrone monomer, a polyaldehyde monomer, a polyketone monomer, and a polyethylenically unsaturated monomer.

According to another embodiment, the present invention features a method of preparing a chalcogenic hybrid inorganic/organic polymer (CHIP) composite. The method may comprise preparing a CHIP polymer matrix, providing at least one isorefractive filler having a refractive index (n) similar or identical to that of the CHIP polymer matrix over a range from n=1.3 to 2.7, and blending about 1-95 wt % variable loading of the isorefractive filler with about 5-99 wt % of the CHIP polymer matrix, thereby producing the CHIP composite. Without wishing to limit the invention to a particular theory or mechanism, the isorefractive filler may be effective for reinforcing a thermomechanical property of the CHIP composite.

In one embodiment, the step of preparing the CHIP polymer matrix may comprise providing at least about 35 wt % of elemental sulfur, heating the elemental sulfur to form molten sulfur, adding at least 35 wt % of elemental selenium ($Se_8$) to the molten sulfur to form a liquid selenium sulfur mixture, adding about 5-50 wt % of one or more comonomers to the liquid selenium sulfur mixture, and polymerizing the comonomers with the liquid selenium sulfur mixture to form the CHIP polymer matrix.

In a further embodiment, the CHIP polymer matrix may be heated until the CHIP polymer matrix is substantially vitrified. In some embodiments, the one or more comonomers are selected from a group consisting of amine comonomers, thiol comonomers, sulfide comonomers, alkynylly unsaturated comonomers, epoxide comonomers, nitrone comonomers, aldehyde comonomers, ketone comonomers, thiirane comonomers, ethylenically unsaturated comonomers, styrenic comonomers, vinylic comonomers, methacrylate comonomers, acrylonitrile comonomers, allylic monomers, acrylate monomers, vinylpyridine monomers, isobutylene monomers, maleimide monomers, norbornene monomers, monomers having at least one vinyl ether moiety, and monomers having at least one isopropenyl moiety In one embodiment, preparing the CHIP polymer matrix may comprise providing at least about 50 wt % of elemental sulfur. In another embodiment, preparing the CHIP polymer matrix may comprise adding at least about 50 wt % of elemental selenium. In a further embodiment, the CHIP polymer matrix may comprise about 35-50 wt % of elemental sulfur, about 35-50 wt % of elemental selenium, and about 15-25 wt % of the comonomers.

According to another embodiment, the step of preparing the CHIP polymer matrix may comprise providing at least about 35 wt % of one or more chalcogenic monomers; adding about 5-50 wt % of one or more comonomers to the sulfur monomers, wherein the one or more comonomers are selected from a group consisting of amine comonomers, thiol comonomers, sulfide comonomers, alkynylly unsaturated comonomers, epoxide comonomers, nitrone comonomers, aldehyde comonomers, ketone comonomers, thiirane comonomers, ethylenically unsaturated comonomers, styrenic comonomers, vinylic comonomers, methacrylate comonomers, acrylonitrile comonomers, allylic monomers, acrylate monomers, vinylpyridine monomers, isobutylene monomers, maleimide monomers, norbornene monomers, monomers having at least one vinyl ether moiety, and monomers having at least one isopropenyl moiety; and polymerizing the comonomers with the sulfur monomers to form the CHIP polymer matrix. In some embodiments, the chalcogenic monomers may comprise elemental sulfur, a liquid polysulfide, a liquid chalcogenide polymer, an oligomer containing sulfur, an oligomer containing sulfur and selenium units, or combinations thereof.

In other embodiments, the CHIP polymer matrix may be further polymerized with one or more termonomers selected from a group consisting of a vinyl monomer, an isopropenyl monomer, an acryl monomer, a methacryl monomer, an unsaturated hydrocarbon monomer, an epoxide monomer, a thiirane monomer, an alkynyl monomer, a diene monomer, a butadiene monomer, an isoprene monomer, a norbornene monomer, an amine monomer, a thiol monomer, a sulfide monomer, an alkynylly unsaturated monomer, a nitrone monomer, an aldehyde monomer, a ketone monomer, an ethylenically unsaturated monomer, and a styrenic monomer.

In still other embodiments, the CHIP polymer matrix may be further polymerized with one or more polyfunctional monomers selected from a group consisting of a polyvinyl monomer, a polyisopropenyl monomer, a polyacryl monomer, a polymethacryl monomer, a polyunsaturated hydrocarbon monomer, a polyepoxide monomer, a polythiirane monomer, a polyalkynyl monomer, a polydiene monomer, a polybutadiene monomer, a polyisoprene monomer, a polynorbornene monomer, a polyamine monomer, a polythiol monomer, a polysulfide monomer, a polyalkynylly unsaturated monomer, a polynitrone monomer, a polyaldehyde monomer, a polyketone monomer, and a polyethylenically unsaturated monomer.

In one embodiment, the chalcogenic monomers may comprise one or more cyclic selenium sulfide monomers having the formula $Se_nS_{(6-n)}$. In another embodiment, the cyclic selenium sulfide monomers can include any isomer of the formula. In some embodiments, n in an integer that can range from 1 to 7. For example, when n=2, the cyclic selenium sulfide monomers have the formula $Se_2S_6$. As another example, when n=3, the cyclic selenium sulfide monomers have the formula $Se_3S_5$. Preferably, the one or more cyclic selenium sulfide monomers can comprise all possible isomers of a specific formula. In alternative embodiments, the selenium sulfide monomers can be of the formula $Se_nS_m$, wherein n ranges from 1 to 7 and m ranges from 1 to 7, wherein the selenium sulfide monomers are not necessarily cyclic. In one embodiment, assuming that n=7, i.e. $Se_7S$, then the cyclic selenium sulfide monomers may comprise at most about 70 wt % of selenium.

In one embodiment, any of the CHIP polymer matrixes described herein may comprise one or more cyclic selenium sulfide monomers at a range of about 5 to 10 wt %, or about 10 to 20 wt %, or about 20 to 30 wt %, or about 30 to 40 wt %, or about 40 to 50 wt %, or about 50 to 60 wt %, or about 60 to 70 wt % of the CHIP polymer matrix. In another embodiment, the cyclic selenium sulfide monomers may comprise selenium units of at most about 20 wt %, or at most about 30 wt %, or at most about 40 wt % or at most about 50 wt %, or at most about 60 wt %, or at most about 70 wt % of the cyclic selenium sulfur monomers. In a further embodiment, the cyclic selenium sulfide monomers comprises at most about 70 wt % of selenium.

In some embodiments, any of the CHIP polymer matrixes described herein may further comprise about 5-50 wt % of chalcogenic monomers. In other embodiments, the chalcogenic monomers can be at a range of about 5 to 10 wt %, or about 10 to 20 wt %, or about 20 to 30 wt %, or about 30 to 40 wt %, or about 40 to 50 wt % of the CHIP polymer matrix.

In other embodiments, any of the CHIP polymer matrixes described herein may comprise the one or more comonomers are at a range of about 5 to 10 wt %, or about 10 to 20 wt %, or about 20 to 30 wt %, or about 30 to 40 wt %, or about 40 to 50 wt % of the CHIP polymer matrix.

In other embodiments, any of the CHIP polymer matrixes described herein may further comprise about 5-50 wt % of elemental sulfur ($S_8$). In other embodiments, the elemental sulfur can be at a range of about 5 to 10 wt %, or about 10 to 20 wt %, or about 20 to 30 wt %, or about 30 to 40 wt %, or about 40 to 50 wt % of the CHIP polymer matrix.

In still other embodiments, any of the CHIP polymer matrixes described herein may further comprise about 5-50 wt % of elemental selenium ($Se_8$). In further embodiments, the elemental selenium can be at a range of about 5 to 10 wt %, or about 10 to 20 wt %, or about 20 to 30 wt %, or about 30 to 40 wt %, or about 40 to 50 wt % of the CHIP polymer matrix. For instance, the CHIP polymer matrix may comprise 30 wt % S, 35 wt % cyclic selenium-sulfide, and 35 wt % 1,3 diisopropenyl benzene.

In some embodiments, any of the CHIP polymer matrixes described herein comprises at least about 50 wt % sulfur monomers. In other embodiments, the one or more comonomers are at a range of about 5 to 10 wt %, or about 10 to 20 wt %, or about 20 to 30 wt %, or about 30 to 40 wt %, or about 40 to 50 wt % of the CHIP polymer matrix. In still other embodiments, the CHIP polymer matrix may further comprise at least about 35 wt %, or at least about 40 wt %, or at least about 50 wt % of elemental selenium ($Se_8$).

In some preferred embodiments, any of the CHIP composites described herein may comprise about 5-99 wt % of the CHIP polymer matrix. In some embodiments, the CHIP polymer matrix may be at a range of about 5 to 10 wt %, or about 10 to 20 wt %, or about 20 to 30 wt %, or about 30 to 40 wt %, or about 40 to 50 wt %, or about 50 to 60 wt %, or about 60 to 70 wt %, or about 70 to 80 wt %, or about 80 to 90 wt %, or about 90 to 99 wt % of the CHIP composite.

In other preferred embodiments, any of the CHIP composites described herein may comprise about 1-95 wt % of the isorefractive filler. In some embodiments, the isorefractive filler may be at a range of about 1 to 10 wt %, or about 10 to 20 wt %, or about 20 to 30 wt %, or about 30 to 40 wt %, or about 40 to 50 wt %, or about 50 to 60 wt %, or about 60 to 70 wt %, or about 70 to 80 wt %, or about 80 to 90 wt %, or about 90 to 95 wt % of the CHIP composite.

In preferred embodiments, any of the CHIP polymer matrixes described herein can have a high refractive index of at least about 1.6. In some embodiments, the refractive index of the isorefractive filler may be at least about 1.6. In other embodiments, the isorefractive filler may comprise alumina ($Al_2O_3$), titania ($TiO_2$), aluminium-doped zinc oxide (Al-doped ZnO), or other refractive index-matched metal oxides, or metal chalcogenide particulates. In other embodiments, the isorefractive filler can have an average particle size of about 1 nm to 500 μm.

In some embodiments, the isorefractive filler comprises refractive index-matched metal oxides chosen from silica, polysilsesquioxanes, zinc oxide (ZnO), iron oxides ($Fe_xO_y$), cobalt oxides, and ternary or complex oxides. In other embodiments, the isorefractive filler comprises metal chalcogenide particulates, when sold metal chalcogenide is cadmium sulphide (CdS), cadmium diselenide ($CdSe_2$), cadmium telluride (CdTe), molybdenum disulfide ($MoS_2$), or tungsten disulfide ($WS_2$). In further embodiments, the isorefractive filler comprises a metal, such as Au, Pt, Ag, or other precious group metals. In some embodiments, the isorefractive filler particles may be 1 nm or larger.

In one embodiment, the refractive index of alumina may be about 1.65-2.2. In another embodiment, the refractive index of titania may be about 1.65-2.2. In yet another embodiment, the Al-doped ZnO the refractive index of Al-doped ZnO is at least about 1.6. In a further embodiment, the Al-doped ZnO may comprise about 2-10 wt % Al. For example, the Al-doped ZnO may comprise about 10 wt % Al doped in the ZnO.

The composite material of the present invention possesses both excellent optical properties with improved mechanical properties by combining the CHIP polymer matrix with isorefractive fillers. Without wishing to limit the invention to a particular theory or mechanism, the inventors have identified appropriate fillers, i.e. based on composition and particle size, and applied appropriate surface treatment on filter particle to enable efficient dispersion in the CHIP polymer matrix.

In preferred embodiments, any of the CHIP composites described herein may be used to prepare optical substrates and devices. For example, a substrate produced from the CHIP composite may be substantially transparent in an infrared or visible spectrum. In one embodiment, the substrate may be substantially transparent in a spectrum having a wavelength range of about 1000-1500 nm. In another embodiment, the substrate may be substantially transparent in a spectrum having a wavelength range of about 3000-

5000 nm. In yet another embodiment, the substrate may be substantially transparent in a spectrum having a wavelength range of about 5-10 microns.

In some embodiments, the substrate may be a film, a lens, or a free-standing object. Preferably, the substrate can have a refractive index of about 1.7-2.6 at a wavelength in a range of about 500 nm to about 8 μm. In other embodiments, the substrate is an optical device component configured for use as a transmitting material in an infrared imaging device. Examples of the optical device component include, but are not limited to, lenses, windows, microlens arrays, waveguides, Bragg reflectors, and optical fibers.

In some embodiments, any of the CHIP polymer matrixes can be modified by reacting an available reactive functional group on the polymeric composition with a second comonomer to form a new polymer material. The technique of reacting may be oxidative coupling, polymerization, or copolymerization.

In some embodiments, the CHIP polymer matrix is a thermoset. In some embodiments, the CHIP polymer matrix is a thermoplastic. In some embodiments, the CHIP polymer matrix is self-healing. In some embodiments, when one or more S—S bonds of the CHIP polymer matrix are broken, the S—S bonds are reconnected by thermal reforming.

In some embodiments, the present invention features a method of repairing an optical substrate, said method comprising providing the optical substrate comprising the CHIP composite having one or more broken S—S bonds, and heat treating the optical substrate at a healing temperature for a period of time in order to reconnect the S—S bonds of the CHIP composite. In some embodiments, the healing temperature is between about 80° C. and 100° C. In some embodiments, the healing temperature is between about 100° C. and 150° C. In some embodiments, the healing temperature is at or near the melting point of the polymeric substrate. In some embodiments, the period of time is between about 4 and 15 hours. In some embodiments, the period of time is between about 8 and 12 hours.

The following is a non-limiting example of a thermal reforming procedure of a self-healing optical substrate.
1. The optical substrate having a crack is placed in an oven.
2. The optical substrate is heated at about 100° C. for about 3 hrs.
3. The optical substrate is inspected to ensure that it is completely self-healed.

Because both anionic and radical polymerization can occur in the polymerization reaction mixtures, any desirable combination of amine comonomers, thiol comonomers, sulfide comonomers, alkynylly unsaturated comonomers, epoxide comonomers, nitrone comonomers, aldehyde comonomers, ketone comonomers, thiirane comonomers, ethylenically unsaturated comonomers, styrenic comonomers, vinylic comonomers, methacrylate comonomers, and acrylonitrile comonomers can be used in the same polymer. As non-limiting examples, in one embodiment of the invention, the one or more monomers are a combination of one or more amine monomers and one or more styrenic monomers.

The person of skill in the art will select monomers and relative ratios thereof in order to provide the desired properties to the polymer. In certain embodiments, the one or more monomers include one or more polyfunctional monomers, optionally in combination with one or more monofunctional monomers. A polyfunctional monomer is one that includes more than one (e.g., 2, or 3) polymerizable amine, thiol, sulfide, alkynylly unsaturated, nitrone and/or nitroso, aldehyde, ketone, thiirane, ethylenically unsaturated, and/or epoxide moieties. Polyfunctional monomers can be used to cross-link selenium-sulfide or sulfur chains to adjust the properties of the polymer, as would be understood by the person of skill in the art. The multiple polymerizable groups of a polyfunctional monomer can be the same or different. For example, a polyfunctional monomer can be a polyvinyl monomer (e.g., divinyl, trivinyl), a polyisopropenyl monomer (e.g., diisoprenyl, trilsoprenyl), a polyacryl monomer (e.g., diacryl, triacryl), a polymethacryl monomer (e.g., dimethacryl, trimethacryl), a polyunsaturated hydrocarbon monomer (e.g., diunsaturated, triunsaturated), a polyepoxide monomer (e.g., diepoxide, triepoxide), a polythiirane monomer (e.g., dithiirane, trithiirane), a polyalkynyl monomer, a polydiene monomer, a polybutadiene monomer, a polyisoprene monomer, a polynorbornene monomer, a polyamine monomer, a polythiol monomer, a polysulfide monomer, a polyalkynylly unsaturated monomers, a polynitrone monomers, a polyaldehyde monomers, a polyketone monomers, and a polyethylenically unsaturated monomers.

In other embodiments, the one or more polyfunctional can be a divinylbenzene, a diisopropenylbenzene, an alkylene di(meth)acrylate, a bisphenol A di(meth)acrylate, a terpene, a carotene, a divinyl (hetero)aromatic compound and a diisopropenyl (hetero)aromatic compound.

In some embodiments, the one or more polyfunctional monomers are at a level of about 2 to about 50 wt %, or about 2 to about 10 wt %, or about 10 to about 20 wt %, or about 20 to about 30 wt %, or about 30 to about 40 wt %, or about 40 to about 50 wt % of the CHIP polymer matrix. In some embodiments, the one or more monofunctional monomers are at a level up to about 5 wt %, or about 10 wt %, or about 15 wt % of the CHIP polymer matrix.

Fréchet-type benzyl ether dendrimers bearing styrenic terminal groups are miscible with liquid selenium-sulfide or sulfur and can be used as polyfunctional cross-linkers. In certain embodiments, the one or more polyfunctional monomers include one or more of a divinylbenzene, a diisopropenylbenzene, an alkylene di(meth)acrylate, a bisphenol A di(meth)acrylate, a terpene, a carotene, a divinyl (hetero) aromatic compound, and a diisopropenyl (hetero)aromatic compound. In other embodiments, a polyfunctional monomer can have one or more amine, thiol, sulfide, alkynylly unsaturated, nitrone and/or nitroso, aldehyde, ketone, thiirane, ethylenically unsaturated, and/or epoxide moieties; and one or more amine, thiol, sulfide, alkynylly unsaturated, nitrone and/or nitroso, aldehyde, ketone, thiirane, ethylenically unsaturated, and/or epoxide moieties, wherein the first and second moieties are different. A non-limiting example is a divinylbenzene monoxide.

The CHIP polymer matrix can be made, for example, by polymerization of a molten mixture of selenium sulfide with the comonomers. Thus, in one aspect, the invention provides a method for making an optical CHIP polymer matrix as described above. The method includes heating a mixture of selenium sulfide and the one or more monomers together at a temperature sufficient to initiate polymerization (i.e., through free radical polymerization, through anionic polymerization, or through both, depending on the monomers used). Elemental sulfur or elemental selenium, or a combination thereof, may be added to the selenium sulfide prior to adding the comonomers. For example, in one embodiment, the method includes heating the mixture to a temperature in the range of about 120° C. to about 230° C., e.g., in the range of about 160° C. to about 230° C. The person of skill in the art will select conditions that provide the desired level of polymerization, in certain embodiments, the polymerization reaction is performed under ambient pressure. However, in other embodiments, the polymerization reaction can be performed at elevated pressure (e.g., in a bomb or an autoclave). Elevated pressures can be used to polymerize more volatile monomers, so that they do not vaporize under the elevated temperature reaction conditions.

In certain embodiments, it can be desirable to use a nucleophilic viscosity modifier in liquefying the cyclic selenium sulfide, for example, before adding one or more of the monomers (e.g., before adding any polyfunctional monomer). For example, in certain embodiments, the cyclic selenium sulfide is first heated with a viscosity modifier, then the viscosity-modified selenium sulfide is heated with one or more monomers (e.g., with one or more polyfunctional monomers). The nucleophilic viscosity modifier can be, for example, a phosphorus nucleophile (e.g., a phosphine), a sulfur nucleophile (e.g., a thiol) or an amine nucleophile (e.g., a primary or secondary amine). When cyclic selenium sulfide is heated in the absence of a nucleophilic viscosity modifier, the cyclic selenium sulfide rings can open to form, e.g., diradicals, which can combine to form linear polysulfide chains which can provide a relatively high overall viscosity to the molten material. Nucleophilic viscosity modifiers can break these linear chains into shorter lengths, thereby making shorter poly(selenium sulfides) that lower the overall viscosity of the molten material, making the cyclic selenium sulfide mixture easier to mix with and other species, and easier to stir for efficient processing. Some of the nucleophilic viscosity modifier will react to be retained as a covalently bound part of the polymer, and some will react to form separate molecular species, with the relative amounts depending on nucleophile identity and reaction conditions. While some of the nucleophilic viscosity modifier may end up as a separate molecular species from the polymer chain, as used herein, nucleophilic viscosity modifiers may become part of the polymer. Non-limiting examples of nucleophilic viscosity modifiers include triphenylphosphine, aniline, benzenethiol, and N,N-dimethylaminopyridine. Nucleophilic viscosity modifiers can be used, for example, in an amount up to about 10 wt %, or even up to about 5 wt % of the CHIP polymer matrix. When a nucleophilic viscosity modifier is used, in certain embodiments it can be used in the range of about 5 wt % to about 15 wt % of the CHIP polymer matrix.

In certain embodiments, a monofunctional monomer can be used to reduce the viscosity of the CHIP polymer matrix, for example, before adding other monomers (e.g., before adding any polyfunctional monomer). For example. In certain embodiments, the CHIP polymer matrix is first heated with one or more monofunctional monomers. While not intending to be bound by theory, the inventors surmise that inclusion of monofunctional monomers into the poly(selenium-sulfide) chains disrupts intermolecular associations of the selenium-sulfide and thus decreases the viscosity. The monofunctional monomer can be, for example, a mono(meth)acrylate such as benzyl methacrylate, a mono(oxirane) such as a styrene oxide or a glycidyl phenyl ether, or a mono(thiirane) such as t-butyl thiirane or phenoxymethylthiirane. A monofunctional monomer can be used to modify the viscosity of the CHIP polymer matrix, for example, in an amount up to about 10 wt %, up to about 5 wt %, or even up to about 2 wt % of the CHIP polymer matrix. When a monofunctional monomer can be used to modify the viscosity of the CHIP polymer matrix, in certain embodiments it can be used in the range of about 0.5 wt % to about 5 wt %, or even about 0.5 wt % to about 3 wt % of the CHIP polymer matrix.

Of course, viscosity modification is not required, so in other embodiments the cyclic selenium-sulfide is heated together with the one or more monomers (and particularly with one or more polyfunctional monomers) without viscosity modification. In other embodiments, a solvent, e.g., a halobenzene such as 1,2,4-trichlorobenzene, a benzyl ether, or a phenyl ether, can be used to modify the viscosity of the materials for ease of handling. The solvent can be added, for example, to the cyclic selenium-sulfide before reaction with a monomer in order to reduce its viscosity, or to the polymerized material in order to aid in processing into a desired form factor, A decrease in viscosity at elevated temperatures (e.g., >about 140° C.) can allow sufficient flow.

The polymers described herein can be partially cured to provide a more easily processable material, which can be processed into a desired form (e.g., into a desired shape, such as in the form of a free-standing shape or a device), then fully cured in a later operation. For example, the optical prepolymer can be formed, for example, by conversion of the one or more monomers at a level in the range of about 20 to about 50 mol %. For example, the heating the CHIP composite to form the optical prepolymer can be performed for a time in the range of about 20 seconds to about five minutes, for example, at a temperature in the range of about 175° C. to about 195° C. In one embodiment, heating is performed for less than about 2 minutes at about 185'C. The person of skill in the art will determine the desired level of monomer conversion in the prepolymer stage to yield a processable prepolymer material, and will determine process conditions that can result in the desired level of monomer conversion.

As used herein, the term "about" refers to plus or minus 10% of the referenced number.

Another aspect of the invention pertains to a chalcogenic hybrid inorganic/organic polymer (CHIP) composite comprising:
   a. about 5-99 wt % of a CHIP polymer matrix comprising:
      iv. one or more sulfur monomers derived from elemental sulfur, at a level of at least 35 wt % of the CHIP polymer matrix;
      v. elemental selenium ($Se_8$) at a level of at least 35 wt % of the CHIP polymer matrix; and
      vi. one or more comonomers each selected from a group consisting of amine comonomers, thiol comonomers, sulfide comonomers, alkynylly unsaturated comonomers, epoxide comonomers, nitrone comonomers, aldehyde comonomers, ketone comonomers, thiirane comonomers, ethylenically unsaturated comonomers, styrenic comonomers, vinylic comonomers, methacrylate comonomers, acrylonitrile comonomers, allylic monomers, acrylate monomers, vinylpyridine monomers, isobutylene monomers, maleimide monomers, norbornene monomers, monomers having at least one vinyl ether moiety, and monomers having at least one isopropenyl moiety, at a level in the range of about 5-50 wt % of the CHIP polymer matrix; and
   b. about 1-95 wt % variable loading of at least one isorefractive filler blended into the CHIP polymer matrix;
wherein the isorefractive filler has a refractive index (n) similar or identical to that of the CHIP polymer matrix over a range from n=1.3 to 2.7, and wherein the isorefractive filler is effective for reinforcing a thermomechanical property of the CHIP composite.

In some embodiments, the CHIP composite comprises a CHIP polymer matrix, wherein the CHIP polymer matrix comprises at least about 50 wt % of the sulfur monomers. In some embodiments, the CHIP composite comprises a CHIP polymer matrix, wherein the CHIP polymer matrix comprises at least about 50 wt % of Se8. In further embodiments, the CHIP polymer matrix comprises about 35-50 wt % of sulfur monomers, about 35-50 wt % of elemental selenium, and about 15-25 wt % of the comonomers.

In further embodiments, the present invention is a chalcogenic hybrid inorganic/organic polymer (CHIP) composite comprising:
a. about 5-99 wt % of a CHIP polymer matrix comprising:
 i. one or more chalcogenic monomers at a level of at least 35 wt % of the CHIP polymer matrix; and
 ii. one or more comonomers each selected from a group consisting of amine comonomers, thiol comonomers, sulfide comonomers, alkynylly unsaturated comonomers, epoxide comonomers, nitrone comonomers, aldehyde comonomers, ketone comonomers, thiirane comonomers, ethylenically unsaturated comonomers, styrenic comonomers, vinylic comonomers, methacrylate comonomers, acrylonitrile comonomers, allylic monomers, acrylate monomers, vinylpyridine monomers, isobutylene monomers, maleimide monomers, norbornene monomers, monomers having at least one vinyl ether moiety, and monomers having at least one isopropenyl moiety, at a level in the range of about 5-50 wt % of the CHIP polymer matrix; and
b. about 1-95 wt % variable loading of at least one isorefractive filler blended into the CHIP polymer matrix;
wherein the isorefractive filler has a refractive index (n) similar or identical to that of the CHIP polymer matrix over a range from n=1.3 to 2.7, and wherein the isorefractive filler is effective for reinforcing a thermomechanical property of the CHIP composite.

The CHIP composite of the invention may comprise one or more chalcogenic monomers, wherein the chalcogenic monomers are selected from a group consisting of elemental sulfur, a liquid polysulfide, a liquid chalcogenide polymer, an oligomer containing sulfur, and an oligomer containing sulfur and selenium units. The CHIP composite may include a CHIP polymer matrix, wherein the CHIP polymer matrix has a high refractive index of at least about 1.6. Furthermore, the CHIP composite may include a isorefractive filler, wherein the refractive index of the isorefractive filler is at least about 1.6. In some embodiments, the isorefractive filler is alumina ($Al_2O_3$), titania ($TiO_2$), aluminium-doped zinc oxide (Al-doped ZnO), or other refractive index-matched metal oxides, or metal chalcogenide particulates. In some embodiments, the isorefractive filler particles may be 1 nm or larger.

In further embodiments, the refractive index of alumina is about 1.65-2.2. In further embodiments, the refractive index of titania is about 1.65-2.2.

The CHIP composite of the invention may include Al-doped ZnO, wherein the Al-doped ZnO comprises about 2-10 wt % Al, wherein the refractive index of Al-doped ZnO is at least about 1.6.

The CHIP composite of the invention may include an isorefractive filler, wherein the isorefractive filler has an average particle size of about 1 nm to 500 μm.

In some embodiments, the CHIP composite of the invention includes a CHIP polymer matrix, wherein the CHIP polymer matrix further comprises one or more termonomers selected from a group consisting of a vinyl monomer, an isopropenyl monomer, an acryl monomer, a methacryl monomer, an unsaturated hydrocarbon monomer, an epoxide monomer, a thiirane monomer, an alkynyl monomer, a diene monomer, a butadiene monomer, an isoprene monomer, a norbornene monomer, an amine monomer, a thiol monomer, a sulfide monomer, an alkynylly unsaturated monomer, a nitrone monomer, an aldehyde monomer, a ketone monomer, an ethylenically unsaturated monomer, and a styrenic monomer.

The CHIP polymer matrix may further comprise one or more polyfunctional monomers selected from a group consisting of a polyvinyl monomer, a polyisopropenyl monomer, a polyacryl monomer, a polymethacryl monomer, a polyunsaturated hydrocarbon monomer, a polyepoxide monomer, a polythiirane monomer, a polyalkynyl monomer, a polydiene monomer, a polybutadiene monomer, a polyisoprene monomer, a polynorbornene monomer, a polyamine monomer, a polythiol monomer, a polysulfide monomer, a polyalkynylly unsaturated monomer, a polynitrone monomer, a polyaldehyde monomer, a polyketone monomer, and a polyethylenically unsaturated monomer.

The CHIP composite of the invention may include a substrate produced from the CHIP composite, wherein the substrate produced from the CHIP composite is substantially transparent in an infrared or visible spectrum.

In some embodiments, the substrate is substantially transparent in a spectrum having a wavelength range of about 1000-1500 nm. Further, the substrate may substantially transparent in a spectrum having a wavelength range of about 3000-5000 nm. In further embodiments, the substrate is substantially transparent in a spectrum having a wavelength range of about 5-10 microns. The substrate may be a film, a lens, or a free-standing object, wherein the substrate has a refractive index of about 1.7-2.6 at a wavelength in a range of about 500 nm to about 8 μm.

Furthermore, the substrate may be an optical device component configured for use as a transmitting material in an infrared imaging device. The optical device component may be a lens, a window, a microlens array, a waveguide, a Bragg reflector, optical sensor, or an optical fiber.

Another aspect of the invention pertains to a method of preparing a chalcogenic hybrid inorganic/organic polymer (CHIP) composite, the method comprising:
preparing a CHIP polymer matrix, comprising:
 providing at least about 35 wt % of elemental sulfur;
 heating the elemental sulfur to form molten sulfur;
 adding at least 35 wt % of elemental selenium ($Se_8$) to the molten sulfur to form a liquid selenium sulfur mixture;
 adding about 5-50 wt % of one or more comonomers to the liquid selenium sulfur mixture, wherein the one or more comonomers are selected from a group consisting of amine comonomers, thiol comonomers, sulfide comonomers, alkynylly unsaturated comonomers, epoxide comonomers, nitrone comonomers, aldehyde comonomers, ketone comonomers, thiirane comonomers, ethylenically unsaturated comonomers, styrenic comonomers, vinylic comonomers, methacrylate comonomers, acrylonitrile comonomers, allylic monomers, acrylate monomers, vinylpyridine monomers, isobutylene monomers, maleimide monomers, norbornene monomers, monomers having at least one vinyl ether moiety, and monomers having at least one isopropenyl moiety; and
polymerizing the comonomers with the liquid selenium sulfur mixture to form the CHIP polymer matrix; and providing at least one isorefractive filler, wherein the isorefractive filler has a refractive index (n) similar or identical to that of the CHIP polymer matrix over a range from n=1.3 to 2.7;

blending about 1-95 wt % variable loading of the isorefractive filler with about 5-99 wt % of the CHIP polymer matrix, thereby producing the CHIP composite, wherein the isorefractive filler is effective for reinforcing a thermomechanical property of the CHIP composite.

In some embodiments, the invention encompasses a method involving preparing a CHIP polymer matrix, wherein preparation of the CHIP polymer matrix further comprises heating the CHIP polymer matrix until the CHIP polymer matrix is substantially vitrified. In further embodiments, preparation of the CHIP polymer matrix comprises providing at least about 50 wt % of elemental sulfur. In further embodiments, preparation of the CHIP polymer matrix comprises adding at least about 50 wt % of elemental selenium. The CHIP polymer matrix may comprise about 35-50 wt % of elemental sulfur, about 35-50 wt % of elemental selenium, and about 15-25 wt % of the comonomers.

Another aspect of the invention pertains to a method of preparing a chalcogenic hybrid inorganic/organic polymer (CHIP) composite, the method comprising:

preparing a CHIP polymer matrix, comprising:
providing at least about 35 wt % of one or more chalcogenic monomers;
adding about 5-50 wt % of one or more comonomers to the sulfur monomers, wherein the one or more comonomers are selected from a group consisting of amine comonomers, thiol comonomers, sulfide comonomers, alkynylly unsaturated comonomers, epoxide comonomers, nitrone comonomers, aldehyde comonomers, ketone comonomers, thiirane comonomers, ethylenically unsaturated comonomers, styrenic comonomers, vinylic comonomers, methacrylate comonomers, acrylonitrile comonomers, allylic monomers, acrylate monomers, vinylpyridine monomers, isobutylene monomers, maleimide monomers, norbornene monomers, monomers having at least one vinyl ether moiety, and monomers having at least one isopropenyl moiety; and
polymerizing the comonomers with the sulfur monomers to form the CHIP polymer matrix; and
providing at least one isorefractive filler, wherein the isorefractive filler has a refractive index (n) similar or identical to that of the CHIP polymer matrix over a range from n=1.3 to 2.7;
blending about 1-95 wt % variable loading of the isorefractive filler with about 5-99 wt % of the CHIP polymer matrix, thereby producing the CHIP composite, wherein the isorefractive filler is effective for reinforcing a thermomechanical property of the CHIP composite.

In some embodiments, the method involves providing at least about 35 wt % of one or more chalcogenic monomers, wherein the chalcogenic monomers are selected from a group consisting of elemental sulfur, a liquid polysulfide, a liquid chalcogenide polymer, an oligomer containing sulfur, and an oligomer containing sulfur and selenium units.

In some embodiments, the method involves a CHIP polymer matrix, wherein the CHIP polymer matrix has a high refractive index of at least about 1.6.

In some embodiments, the method involves a isorefractive filler, wherein the refractive index of the isorefractive filler is at least about 1.6. In further embodiments, the isorefractive filler is alumina ($Al_2O_3$), titania ($TiO_2$), aluminium-doped zinc oxide (Al-doped ZnO), or other refractive index-matched metal oxides, or metal chalcogenide particulates. In further embodiments, the refractive index of alumina is about 1.65-2.2. In further embodiments, the refractive index of titania is about 1.65-2.2. In further embodiments, the Al-doped ZnO comprises about 2-10 wt % Al, wherein the refractive index of Al-doped ZnO is at least about 1.6. In further embodiments, the isorefractive filler has an average particle size of about 1 nm to 500 μm.

In some embodiments, the method of preparing a chalcogenic hybrid inorganic/organic polymer (CHIP) composite further comprises polymerizing the CHIP polymer matrix with one or more termonomers selected from a group consisting of a vinyl monomer, an isopropenyl monomer, an acryl monomer, a methacryl monomer, an unsaturated hydrocarbon monomer, an epoxide monomer, a thiirane monomer, an alkynyl monomer, a diene monomer, a butadiene monomer, an isoprene monomer, a norbornene monomer, an amine monomer, a thiol monomer, a sulfide monomer, an alkynylly unsaturated monomer, a nitrone monomer, an aldehyde monomer, a ketone monomer, an ethylenically unsaturated monomer, and a styrenic monomer.

In some embodiments, the method of preparing a chalcogenic hybrid inorganic/organic polymer (CHIP) composite further comprises polymerizing the CHIP polymer matrix with one or more polyfunctional monomers selected from a group consisting of a polyvinyl monomer, a polyisopropenyl monomer, a polyacryl monomer, a polymethacryl monomer, a polyunsaturated hydrocarbon monomer, a polyepoxide monomer, a polythiirane monomer, a polyalkynyl monomer, a polydiene monomer, a polybutadiene monomer, a polyisoprene monomer, a polynorbornene monomer, a polyamine monomer, a polythiol monomer, a polysulfide monomer, a polyalkynylly unsaturated monomer, a polynitrone monomer, a polyaldehyde monomer, a polyketone monomer, and a polyethylenically unsaturated monomer.

The method of preparing a chalcogenic hybrid inorganic/organic polymer (CHIP) composite may involve a substrate, wherein the substrate produced from the CHIP composite is substantially transparent in an infrared or visible spectrum.

The method of preparing a chalcogenic hybrid inorganic/organic polymer (CHIP) composite may involve a substrate, wherein the substrate is substantially transparent in a spectrum having a wavelength range of about 1000-1500 nm.

The method of preparing a chalcogenic hybrid inorganic/organic polymer (CHIP) composite may involve a substrate, wherein the substrate is substantially transparent in a spectrum having a wavelength range of about 3000-5000 nm.

The method of preparing a chalcogenic hybrid inorganic/organic polymer (CHIP) composite may involve a substrate, wherein the substrate is substantially transparent in a spectrum having a wavelength range of about 5-10 microns.

The method of preparing a chalcogenic hybrid inorganic/organic polymer (CHIP) composite may involve a substrate, wherein the substrate is a film, a lens, or a free-standing object, wherein the substrate has a refractive index of about 1.7-2.6 at a wavelength in a range of about 500 nm to about 8 μm.

The method of preparing a chalcogenic hybrid inorganic/organic polymer (CHIP) composite may involve a substrate, wherein the substrate is an optical device component configured for use as a transmitting material in an infrared imaging device.

The method of preparing a chalcogenic hybrid inorganic/organic polymer (CHIP) composite may involve an optical device component, wherein the optical device component is a lens, a window, a microlens array, a waveguide, a Bragg reflector, or an optical fiber.

3.0 Solution Processable Chalcogenide Hybrid Inorganic/Organic Polymers (CHIPS) For Optical Short-Wave Infrared And Mid-infrared Mirrors And Reflectors As used herein, the term "photonic crystal" is used in its conventional meaning to refer to optical structures having a periodic arrangement of materials with different refractive indices.

As used herein, the term "disposed" refers to where one or more polymers, materials and/or composites is "deposited" or "spatially positioned" relative to another polymer and/or materials and/or composites or other substrate. For example, the invention encompasses a photonic crystal comprising at least one layer of a first polymer having a high refractive index, and at least one layer of a second polymer having a low refractive index, wherein the layer of the second polymer is "deposited" or "spatially positioned over or below the layer of the first polymer.

As used herein, sulfur can be provided as elemental sulfur, for example, in powdered form. Under ambient conditions, elemental sulfur primarily exists in an eight-membered ring form (S8) which melts at temperatures in the range of 120° C.-130° C. and undergoes an equilibrium ring-opening polymerization (ROP) of the S8 monomer into a linear polysulfane with diradical chain ends. As the person of skill in the art will appreciate, while S8 is generally the most stable, most accessible and cheapest feedstock, many other allotropes of sulfur can be used (such as other cyclic allotropes, derivable by melt-thermal processing of S8). Any sulfur species that yield diradical or anionic polymerizing species when heated as described herein can be used in practicing the present invention.

As used herein, a "styrenic comonomer" is a monomer that has a vinyl functional group. The styrenic comonomer may comprise a styrene and at least one reactive functional group. As known to one of ordinary skill in the art, a styrene is a derivative of benzene ring that has a vinylic moiety. The sulfur diradicals can link to the vinylic moieties of the styrenic commoners to form the sulfur-styrenic polymer. In certain embodiments, the reactive functional group may be a halogen, an alkyl halide, an alkyl, an alkoxy, an amine, or a nitro functional group. Non-limiting examples of styrenic comonomers include bromostyrene, chlorostyrene, fluorostyrene, (trifluoromethyl)styrene, vinylaniline, acetoxystyrene, methoxystyrene, ethoxystyrene, methylstyrene, nitrostyrene, vinylbenzoic acid, vinylanisole, and vinylbenzyl chloride.

As used herein, the term "amine monomer" is a monomer that has an amine functional group. In one embodiment, aromatic amines and multi-functional amines may be used. Amine monomers include, but are not limited to, aromatic amines, m-phenylenediamine, and p-phenylenediamine. The various types of phenylenediamines are inexpensive reagents due to their wide-spread use in the preparation of many conventional polymers. e.g., polyureas, polyamides As used herein, the term "thiol monomer" is a monomer that has a thiol functional group. Thiol monomers include, but are not limited to, 4,4'-thiobisbenzenethlol and the like. The term "sulfide monomers" are monomers that have sulfide functional groups.

As used herein, an alkynylly unsaturated monomer is a monomer that has an alkynylly unsaturated functional group (i.e. triple bond). The term "alkynylly unsaturated monomer" does not include compounds in which the alkynyl unsaturation is part of a long chain alkyl moiety (e.g., unsaturated fatty acids, or carboxylic salts, or esters such as oleates, and unsaturated plant oils). In one embodiment, aromatic alkynes, both internal and terminal alkynes, multi-functional alkynes may be used. Examples of alkynylly unsaturated monomers include, but are not limited to, ethynylbenzene, 1-phenylpropyne, 1,2-diphenylethyne, 1,4-diethynylbenzene, 1,4-bis(phenylethynyl) benzene, and 1,4-diphenylbuta-1,3-diyne.

As used herein, the term "nitrone monomer" is a monomer that has a nitrone groups. In one embodiment, nitrones, dinitrones, and multi-nitrones may be used. Examples include, but are not limited to, N-benzylidene-2-methylpropan-2-amine oxide.

As used herein, the term "aldehyde monomer" is a monomer that has an aldehyde functional group. In one embodiment, aldehydes, dialdehydes, and multi-aldehydes may be used.

As used herein, the term "ketone monomer" is a monomer that has a ketone functional group. In one embodiment, ketones, di-ketones, and multi-ketones may be used.

As used herein, the term "epoxide monomer" is a monomer that has epoxide functional groups. Non-limiting examples of such monomers include, generally, mono- or polyoxlranylbenzenes, mono- or polyglycidylbenzenes, mono- or polyglycidyloxybenzenes, mono- or polyoxiranyl (hetero)aromatic compounds, mono- or polyglycidyl(hetero) aromatic compounds, mono- or polyglycidyloxy(hetero)aromatic compounds, diglycidyl bisphenol A ethers, mono- or polyglycidyl(cyclo)alkyl ethers, mono- or polyepoxy(cyclo) alkane compounds and oxirane-terminated oligomers. In one preferred embodiment, the epoxide monomers may be benzyl glycidyl ether and tris(4-hydroxyphenyl)methane triglycidyl ether. In certain embodiments, the epoxide monomers may include a (hetero)aromatic moiety such as, for example, a phenyl, a pyridine, a triazine, a pyrene, a naphthalene, or a polycyclic (hetero)aromatic ring system, bearing one or more epoxide groups. For example, in certain embodiments, the one or more epoxide monomers are selected from epoxy(hetero)aromatic compounds, such as styrene oxide and stilbene oxide and (hetero)aromatic glycidyl compounds, such as glycidyl phenyl ethers (e.g., resorcinol diglycidyl ether, glycidyl 2-methylphenyl ether), glycidylbenzenes (e.g., (2,3-epoxypropyl)benzene) and glycidyl heteroaromatic compounds (e.g., N-(2,3-epoxypropyl)phthalimide). In certain desirable embodiments, an epoxide monomer will have a boiling point greater than 180° C. greater than 200° C. or even greater than 230° C. at the pressure at which polymerization is performed (e.g., at standard pressure, or at other pressures).

As used herein, the term "thiirane monomer" is a monomer that has a thirane functional group. Non-limiting examples of thiirane monomers include, generally, mono- or polythiiranylbenzenes, mono- or polythiiranylmethylbenzenes, mono- or polythiiranyl(hetero)aromatic compounds, mono- or polythiiranylmethyl(hetero)-aromatic compounds, dithiiranylmethyl bisphenol A ethers, mono- or polydithiiranyl (cyclo)alkyl ethers, mono- or polyepisulfide(cyclo) alkane compounds, and thiirane-terminated oligomers. In some embodiments, thiirane monomers may include a (hetero)aromatic moiety such as, for example, a phenyl, a pyridine, a triazine, a pyrene, a naphthalene, or a poly cyclic (hetero)aromatic ring system, bearing one or more thiirane groups, in certain desirable embodiments, a thiirane monomer can have a boiling point greater than 180° C., greater than 200° C., or even greater than 230° C. at the pressure at which polymerization is performed (e.g., at standard pressure).

As used herein, an ethylenically unsaturated monomer is a monomer that contains an ethylenically unsaturated functional group (i.e. double bond). The term "ethylenically unsaturated monomer" does not include cyclopentadienyl species such as cyclopentadiene and dicyclopentadiene. The term "ethylenically unsaturated monomer" does not include compounds in which the ethylenic unsaturation is part of a long chain alkyl moiety (e.g. unsaturated fatty acids such as oleates, and unsaturated plant oils).

Non-limiting examples of ethylenically unsaturated monomers include vinyl monomers, acryl monomers, (meth)acryl monomers, unsaturated hydrocarbon monomers, and ethylenically-terminated oligomers. Examples of such monomers include, generally, mono- or polyvinylbenzenes, mono- or polyisopropenylbenzenes, mono- or polyvinyl(hetero)aromatic compounds, mono- or polyisopropenyl(hetero)-aromatic compounds, acrylates, methacrylates, alkylene di(meth)acrylates, bisphenol A di(meth)acrylates, benzyl (meth)acrylates, phenyl(meth)acrylates, heteroaryl (meth)acrylates, terpenes (e.g., squalene) and carotene. In other embodiments, the ethylenically unsaturated monomers may include a (hetero)aromatic moiety such as, for example, phenyl, pyridine, triazine, pyrene, naphthalene, or a polycyclic (hetero)aromatic ring system, bearing one or more vinylic, acrylic or methacrylic substituents. Examples of such monomers include benzyl (meth)acrylates, phenyl (meth)acrylates, divinylbenzenes (e.g., 1,3-divinylbenzene, 1,4-divinylbenzene), isopropenylbenzene, styrenics (e.g., styrene, 4-methylstyrene, 4-chlorostyrene, 2,6-dichlorostyrene, 4-vinylbenzyl chloride), diisopropenylbenzenes (e.g., 1,3-diisopropenylbenzene), vinylpyridines (e.g., 2-vinylpyridine, 4-vinylpyridine), 2,4,6-tris((4-vinylbenzyl)thio)-1,3,5-triazine and divinylpyridines (e.g., 2,5-divinylpyridine). In certain embodiments, the ethylenically unsaturated monomers (e.g., including an aromatic moiety) bear an amino (i.e., primary or secondary) group, a phosphine group or a thiol group. One example of such a monomer is vinyldiphenylphosphine. In certain desirable embodiments, an ethylenically unsaturated monomer will have a boiling point greater than 180° C., greater than 200° C., or even greater than 230° C. at the pressure at which polymerization is performed (e.g., at standard pressure).

As used herein, the term "self-healing" is defined as to enable a material to repair damage with minimum intervention. In some embodiments, mechanisms and techniques to enable self-healing may include covalent bonding, supramolecular chemistry, H-bonding, ionic interactions, π-π stacking, chemo-mechanical repairs focusing on encapsulation, remote self-healing, or shape memory assisted polymers. In one preferred embodiment, self-healing utilizes thermal reformation. As used herein, thermal reformation involves the use of heat to reform the bonds or cross-links of a polymeric material.

As used herein, the term "functional" in correlation with a polymer refers to functional polymers that have specified physical, chemical, biological, pharmacological, or other properties or uses that are determined by the presence of specific chemical functional groups, which are usually dissimilar to those of the backbone chain of the polymer.

As used herein, the term "chalcogenide" refers to a compound containing one or more chalcogen elements. One of ordinary skill in the art will understand that the classical chalcogen elements are sulfur, selenium and tellurium. In accordance with the present invention, the use of chalcogenide refers to compounds and/or polymers containing selenium.

As known to one of ordinary skill in the art, the term "isomer" refers to compounds having the same formula but differ in arrangement. For instance, isomers of cyclic selenium sulfides, such as $Se_2S_6$ and $Se_3S_5$, can have different placements of the Se units in the ring (e.g., S—Se—Se—S or S—Se—S). Isomers of $Se_2Se_6$ include 1,2-isomers, 1,3-isomers, 1,4-isomers, and 1,5-isomers, wherein the numbers refer to the position of the Se units in the eight-membered ring.

As used herein, the term "infrared" (IR) refers to a portion of the electromagnetic spectrum that falls in the range of 700 nm to 1 mm. Subsets of the IR spectrum include near-IR (700 and 1,100 nanometers), shortwave IR (SWIR) (1,100 and 3,000 nanometers), mid-IR (3-8 μm), long-wavelength IR (8-15 μm) and far-IR (15 μm to 1 mm).

As used herein, the terms "those defined above" and "those defined herein" when referring to a variable incorporates by reference the broad definition of the variable as well as any narrow and/or preferred, more preferred and most preferred definitions, if any.

Referring now to FIG. 7-11, in one embodiment, the present invention features a photonic crystal comprising at least one layer of a first polymer having a high refractive index, and at least one layer of a second polymer having a low refractive index. Preferably, the layer of the second polymer may be disposed over or below the layer of the first polymer. For example, the layer of the second polymer layer is disposed over and contacts the layer of the first polymer. Alternatively, the layer of the first polymer layer is disposed over and contacts the layer of the second polymer. In some embodiments, each layer is a continuous layer. In other embodiments, the photonic crystal reflects at least one bandwidth in a short-wave infrared to mid-infrared spectrum.

In a preferred embodiment, the first polymer has a high refractive index of at least about 1.6. In another embodiment, the second polymer has a low refractive index of about 1.4-1.6.

In one embodiment, the first polymer may comprise a chalcogenic hybrid inorganic/organic polymer (CHIP) material comprising one or more chalcogenic monomers at a level of at least 50 wt % of the CHIP material, and one or more comonomers each selected from a group consisting of amine comonomers, thiol comonomers, sulfide comonomers, alkynylly unsaturated comonomers, epoxide comonomers, nitrone comonomers, aldehyde comonomers, ketone comonomers, thiirane comonomers, ethylenically unsaturated comonomers, styrenic comonomers, vinylic comonomers, methacrylate comonomers, acrylonitrile comonomers, allylic monomers, acrylate monomers, vinylpyridine monomers, isobutylene monomers, maleimide monomers, norbornene monomers, monomers having at least one vinyl ether moiety, and monomers having at least one isopropenyl moiety, at a level in the range of about 5-50 wt % of the CHIP material. In preferred embodiments, the CHIP material is melt and/or solution processable.

In some embodiments, the chalcogenic monomers are selected from a group consisting of elemental sulfur, a liquid polysulfide, an oligomer containing sulfur, and an oligomer containing sulfur and selenium units. In other embodiments, the chalcogenic monomers may comprise sulfur monomers derived from elemental sulfur, and elemental selenium ($Se_8$) or selenium sulfide, or a combination thereof.

In another embodiment, the second polymer is cellulose acetate or poly(vinyl alcohol). However, the second polymer may be any other polymer having a low refractive index relative to the CHIP material.

In some embodiments, a thickness of the first polymer layer is about 1-5000 nm. For example, the thickness of the first polymer layer is about 200-800 nm. In other embodiments, a thickness of the second polymer layer is about 1-5000 nm. For example, the thickness of the second polymer layer is about 200-800 nm.

In other embodiments, the photonic crystal may further comprise a plurality of alternating layers of the first polymer and the second polymer. The number of alternating layers can range from about 2-100.

According to another embodiment, the present invention features a photonic crystal device comprising a plurality of alternating layers of a first polymer having a high refractive index and a second polymer having a low refractive index. In some embodiments, the plurality of alternating layers can reflect at least one band in the short-wave infrared to mid-infrared spectrum. Examples of the photonic crystal device include, but are not limited to, a Bragg reflector, a dielectric mirror, a narrowband filter, a notch filter, a broadband filter, a spike filter, IR refractive coatings, IR reflective paints for heat management applications, reflective coatings for the infrared (IR), and a Fabry-Perot etalon. In one embodiment, the first polymer can have a high refractive index of at least about 1.6. In another embodiment, the second polymer can have a low refractive index of about 1.4-1.6.

In some embodiments, the first polymer may comprise a chalcogenic hybrid inorganic/organic polymer (CHIP) material comprising one or more chalcogenic monomers at a level of at least 50 wt % of the CHIP material, and one or more comonomers each selected from a group consisting of amine comonomers, thiol comonomers, sulfide comonomers, alkynylly unsaturated comonomers, epoxide comonomers, nitrone comonomers, aldehyde comonomers, ketone comonomers, thiirane comonomers, ethylenically unsaturated comonomers, styrenic comonomers, vinylic comonomers, methacrylate comonomers, acrylonitrile comonomers, allylic monomers, acrylate monomers, vinylpyridine monomers, isobutylene monomers, maleimide monomers, norbornene monomers, monomers having at least one vinyl ether moiety, and monomers having at least one isopropenyl moiety, at a level in the range of about 5-50 wt % of the CHIP material. In preferred embodiments, the CHIP material is melt and/or solution processable.

In other embodiments, the chalcogenic monomers are selected from a group consisting of elemental sulfur, a liquid polysulfide, an oligomer containing sulfur, and an oligomer containing sulfur and selenium units. In further embodiments, the chalcogenic monomers may comprise sulfur monomers derived from elemental sulfur, and elemental selenium ($Se_8$) or selenium sulfide, or a combination thereof.

In still other embodiments, the second polymer is cellulose acetate or poly(vinyl alcohol). However, the second polymer may be any other polymer having a low refractive index relative to the CHIP material. In addition to at least one layer of a first polymer and at least one layer of a second polymer, in some embodiments, the photonic crystal disclosed herein may include the introduction of third, or other layers composed of materials with different refractive index. Furthermore, the introduction of third, or other layers composed of materials with different refractive index may be introduced to modulate the reflectivity across the NIR, SWIR and mid-IR.

In some embodiments, a thickness of each alternating layer can range from about 1-5000 nm. For example, the thickness of each alternating layer ranges from about 200-800 nm. In other embodiments, the number of the alternating layers ranges from about 2 to 100 layers.

According to yet another embodiment, the present invention features a method of fabricating a photonic crystal device. Examples of the photonic crystal device include, but are not limited to a Bragg reflector, a dielectric mirror, a narrowband filter, a notch filter, a broadband filter, a spike filter, IR refractive coatings, IR reflective paints for heat management applications, reflective coatings for the infrared (IR), and a Fabry-Perot etalon.

In one embodiment, the method may comprise providing a surface layer, and depositing a plurality of alternating layers of a first polymer and a second polymer on said surface layer. Preferably, the first polymer has a high refractive index, and the second polymer has a low refractive index. For example, the first polymer can have a high refractive index of at least about 1.6, whereas the second polymer can have a low refractive index of about 1.4-1.6. In other preferred embodiments, the plurality of alternating layers can reflect at least one bandwidth in a short-wave infrared to mid-infrared spectrum.

In some embodiments, the first polymer may comprise a chalcogenic hybrid inorganic/organic polymer (CHIP) material comprising one or more chalcogenic monomers at a level of at least 50 wt % of the CHIP material, and one or more comonomers each selected from a group consisting of amine comonomers, thiol comonomers, sulfide comonomers, alkynylly unsaturated comonomers, epoxide comonomers, nitrone comonomers, aldehyde comonomers, ketone comonomers, thiirane comonomers, ethylenically unsaturated comonomers, styrenic comonomers, vinylic comonomers, methacrylate comonomers, acrylonitrile comonomers, allylic monomers, acrylate monomers, vinylpyridine monomers, isobutylene monomers, maleimide monomers, norbornene monomers, monomers having at least one vinyl ether moiety, and monomers having at least one isopropenyl moiety, at a level in the range of about 5-50 wt % of the CHIP material. In preferred embodiments, the CHIP material is melt and/or solution processable.

In other embodiments, the chalcogenic monomers are selected from a group consisting of elemental sulfur, a liquid polysulfide, an oligomer containing sulfur, and an oligomer containing sulfur and selenium units. In further embodiments, the chalcogenic monomers may comprise sulfur monomers derived from elemental sulfur, and elemental selenium ($Se_8$) or selenium sulfide, or a combination thereof.

In some other embodiments, the second polymer is cellulose acetate or poly(vinyl alcohol). However, the second polymer may be any other polymer having a low refractive index relative to the CHIP material.

In one embodiment, a thickness of each alternating layer can range from about 1-5000 nm. For example, the thickness of each alternating layer ranges from about 200-800 nm. In another embodiment, the number of the alternating layers ranges from about 2 to 100 layers.

According to another embodiment of the present invention, the method of fabricating the photonic crystal device may comprise providing a substrate having a surface layer, preparing a chalcogenic hybrid inorganic/organic polymer (CHIP) material, dissolving the CHIP material in a first solvent to form a first polymeric solution, providing a low refractive index polymer, dissolving the low refractive index polymer in a second solvent to form a second polymeric solution, and spin-coating a plurality of alternating layers of the first polymeric solution and the second polymeric solution on the surface layer of the substrate until a specified number of layers is disposed on the substrate. Spin-coating techniques are known to one of ordinary skill in the art. For instance, melt processing methods, such as, extrusion may also be employed to create these multi-layered films.

In preferred embodiments, the plurality of alternating layers can reflect at least one bandwidth in a short-wave infrared to mid-infrared spectrum. In some embodiments, the CHIP material can have a high refractive index of at least about 1.6. In other embodiments, the low refractive index polymer can have a low refractive index of about 1.4-1.6.

In one embodiment, the number of layers can range from about 10 to 100 layers. In another embodiment, a thickness of each alternating layer can range from about 1-5000 nm. For example, the thickness of each alternating layer can range from about 200-800 nm.

In some embodiments, the step of preparing the CHIP material may comprise providing at least about 50 wt % of one or more chalcogenic monomers; adding about 5-50 wt % of one or more comonomers to the chalcogenic monomers, wherein the one or more comonomers are selected from a group consisting of amine comonomers, thiol comonomers, sulfide comonomers, alkynylly unsaturated comonomers, epoxide comonomers, nitrone comonomers, aldehyde comonomers, ketone comonomers, thiirane comonomers, ethylenically unsaturated comonomers, styrenic comonomers, vinylic comonomers, methacrylate comonomers, acrylonitrile comonomers, allylic monomers, acrylate monomers, vinylpyridine monomers, isobutylene monomers, maleimide monomers, norbornene monomers, monomers having at least one vinyl ether moiety, and monomers having at least one isopropenyl moiety; and polymerizing the comonomers with the chalcogenic monomers to form the CHIP material.

In other embodiments, the chalcogenic monomers are selected from a group consisting of elemental sulfur, a liquid polysulfide, an oligomer containing sulfur, and an oligomer containing sulfur and selenium units. In further embodiments, the chalcogenic monomers may comprise sulfur monomers derived from elemental sulfur, and elemental selenium ($Se_8$) or selenium sulfide, or a combination thereof.

In other embodiments, the second polymer is cellulose acetate or poly(vinyl alcohol). However, the second polymer may be any other polymer having a low refractive index relative to the CHIP material.

In one embodiment, the first solvent may be an organic solvent, such as a halobenzene. In another embodiment, the second solvent is an aqueous or organic solvent. For example, the second solvent can be water. However, the first and second solvents are not limited to the aforementioned examples. Preferably, the first and second solvents may be any combination of solvents with the proviso that the second solvent is orthogonal to the first solvent such that the CHIP material is insoluble in the second solvent and the low refractive index polymer is insoluble in the first solvent.

According to another embodiment of the present invention, the method of fabricating the photonic crystal device may comprise preparing the CHIP material as previously described, melting the CHIP material to form a first polymeric melt solution, melting the low refractive index polymer to form a second polymeric melt solution, and performing a multilayered co-extrusion technique utilizing the first polymeric melt solution and the second polymeric melt solution to produce the photonic crystal device comprising a plurality of alternating layers of the CHIP material and the low refractive index polymer. Examples of multilayered co-extrusion techniques can be found in U.S. Pat. Nos. 5,628,950, 5,628,950, and 8,215,940, the specifications of which are incorporated herein in their entirety by reference.

In preferred embodiments, the plurality of alternating layers can reflect at least one bandwidth in a short-wave infrared to mid-infrared spectrum. In some embodiments, the number of layers can range from about 10 to 100 layers. In another embodiment, the thickness of each alternating layer can range from about 1-5000 nm. For example, the thickness of each alternating layer can range from about 200-800 nm.

In some embodiments, any of the CHIP materials described herein may further comprise at least about 35 wt % of chalcogenic monomers. In other embodiments, the chalcogenic monomers can be at a range of about 35 to 50 wt %, or about 50 to 60 wt %, or about 60 to 70 wt %, or about 70 to 80 wt %, or about 80 to 99 wt % of the CHIP material.

In other embodiments, any of the CHIP materials described herein may comprise the one or more comonomers are at a range of about 5 to 10 wt %, or about 10 to 20 wt %, or about 20 to 30 wt %, or about 30 to 40 wt %, or about 40 to 50 wt % of the CHIP material.

In one embodiment, the chalcogenic monomers may comprise one or more cyclic selenium sulfide monomers having the formula $Se_nS_{(6-n)}$. In another embodiment, the cyclic selenium sulfide monomers can include any isomer of the formula. In some embodiments, n in an integer that can range from 1 to 7. For example, when n=2, the cyclic selenium sulfide monomers have the formula $Se_2S_6$. As another example, when n=3, the cyclic selenium sulfide monomers have the formula $Se_3S_5$. Preferably, the one or more cyclic selenium sulfide monomers can comprise all possible isomers of a specific formula. In alternative embodiments, the selenium sulfide monomers can be of the formula $Se_nS_m$, wherein n ranges from 1 to 7 and m ranges from 1 to 7, wherein the selenium sulfide monomers are not necessarily cyclic. In one embodiment, assuming that n=7, i.e. $Se_7S$, then the cyclic selenium sulfide monomers may comprise at most about 70 wt % of selenium.

In one embodiment, the chalcogenic monomers may comprise one or more cyclic selenium sulfide monomers at a range of about 5 to 10 wt %, or about 10 to 20 wt %, or about 20 to 30 wt %, or about 30 to 40 wt %, or about 40 to 50 wt %, or about 50 to 60 wt %, or about 60 to 70 wt % of the chalcogenic monomers. In another embodiment, the cyclic selenium sulfide monomers may comprise selenium units of at most about 20 wt %, or at most about 30 wt %, or at most about 40 wt % or at most about 50 wt %, or at most about 60 wt %, or at most about 70 wt % of the cyclic selenium sulfide monomers. In a further embodiment, the cyclic selenium sulfide monomers comprises at most about 70 wt % of selenium.

In other embodiments, the chalcogenic monomers may further comprise about 5-90 wt % of elemental sulfur ($S_8$). In other embodiments, the elemental sulfur can be at a range of about 5 to 20 wt %, or about 20 to 40 wt %, or about 40 to 60 wt %, or about 60 to 80 wt %, or about 80 to 90 wt % of the chalcogenic monomers.

In still other embodiments, the chalcogenic monomers may further comprise about 5-90 wt % of elemental selenium ($Se_8$). In further embodiments, the elemental selenium can be at a range of about 5 to 20 wt %, or about 20 to 40 wt %, or about 40 to 60 wt %, or about 60 to 80 wt %, or about 80 to 90 wt % of the chalcogenic monomers. For instance, the CHIP material may comprise 30 wt % S, 35 wt % $Se_8$, and 35 wt % 1,3 diisopropenylbenzene. As another example, the CHIP material may comprise 50 wt % S, 20 wt % $Se_8$, and 30 wt % 1,3 diisopropenylbenzene. In another embodiment, the CHIP material may comprise 42 wt % S, 42 wt % $Se_8$, and 16 wt % 1,3 diisopropenylbenzene.

In some embodiments, any of the CHIP polymer materials can be modified by reacting an available reactive functional group on the polymeric composition with a second comonomer to form a new polymer material. The technique of reacting may be oxidative coupling, polymerization, or copolymerization.

In some embodiments, the CHIP material is a thermoset. In some embodiments, the CHIP material is a thermoplastic. In some embodiments, the CHIP material is self-healing. In some embodiments, when one or more S—S bonds of the CHIP material are broken, the S—S bonds are reconnected by thermal reforming.

Because both anionic and radical polymerization can occur in the polymerization reaction mixtures, any desirable combination of amine comonomers, thiol comonomers, sulfide comonomers, alkynylly unsaturated comonomers, epoxide comonomers, nitrone comonomers, aldehyde comonomers, ketone comonomers, thiirane comonomers, ethylenically unsaturated comonomers, styrenic comonomers, vinylic comonomers, methacrylate comonomers, and acrylonitrile comonomers can be used in the same polymer. As non-limiting examples, in one embodiment of the invention, the one or more monomers are a combination of one or more amine monomers and one or more styrenic monomers.

The person of skill in the art will select monomers and relative ratios thereof in order to provide the desired properties to the polymer. In certain embodiments, the one or more monomers include one or more polyfunctional monomers, optionally in combination with one or more monofunctional monomers. A polyfunctional monomer is one that includes more than one (e.g., 2, or 3) polymerizable amine, thiol, sulfide, alkynylly unsaturated, nitrone and/or nitroso, aldehyde, ketone, thiirane, ethylenically unsaturated, and/or epoxide moieties. Polyfunctional monomers can be used to cross-link with the comonomers or the chalcogenic monomer chains to adjust the properties of the polymer, as would be understood by the person of skill in the art. The multiple polymerizable groups of a polyfunctional monomer can be the same or different. For example, a polyfunctional monomer can be a polyvinyl monomer (e.g., divinyl, trivinyl), a polyisopropenyl monomer (e.g., diisoprenyl, triisoprenyl), a polyacryl monomer (e.g., diacryl, triacryl), a polymethacryl monomer (e.g., dimethacryl, trimethacryl), a polyunsaturated hydrocarbon monomer (e.g., diunsaturated, triunsaturated), a polyepoxide monomer (e.g., diepoxide, triepoxide), a polythiirane monomer (e.g., dithiirane, trithiirane), a polyalkynyl monomer, a polydiene monomer, a polybutadiene monomer, a polyisoprene monomer, a polynorbornene monomer, a polyamine monomer, a polythiol monomer, a polysulfide monomer, a polyalkynylly unsaturated monomers, a polynitrone monomers, a polyaldehyde monomers, a polyketone monomers, and a polyethylenically unsaturated monomers.

In other embodiments, the one or more polyfunctional can be a divinylbenzene, a diisopropenylbenzene, an alkylene di(meth)acrylate, a bisphenol A di(meth)acrylate, a terpene, a carotene, a divinyl (hetero)aromatic compound and a diisopropenyl (hetero)aromatic compound.

In some embodiments, the one or more polyfunctional monomers are at a level of about 2 to about 50 wt %, or about 2 to about 10 wt %, or about 10 to about 20 wt %, or about 20 to about 30 wt %, or about 30 to about 40 wt %, or about 40 to about 50 wt % of the CHIP material. In some embodiments, the one or more monofunctional monomers are at a level up to about 5 wt %, or about 10 wt %, or about 15 wt % of the CHIP material.

In other embodiments, the CHIP material may further comprise one or more termonomers selected from a group consisting of a vinyl monomer, an isopropenyl monomer, an acryl monomer, a methacryl monomer, an unsaturated hydrocarbon monomer, an epoxide monomer, a thiirane monomer, an alkynyl monomer, a diene monomer, a butadiene monomer, an isoprene monomer, a norbornene monomer, an amine monomer, a thiol monomer, a sulfide monomer, an alkynylly unsaturated monomer, a nitrone monomer, an aldehyde monomer, a ketone monomer, an ethylenically unsaturated monomer, and a styrenic monomer.

Fréchet-type benzyl ether dendrimers bearing styrenic terminal groups are miscible with the chalcogenic monomers and can be used as polyfunctional cross-linkers. In certain embodiments, the one or more polyfunctional monomers include one or more of a divinylbenzene, a diisopropenylbenzene, an alkylene di(meth)acrylate, a bisphenol A di(meth)acrylate, a terpene, a carotene, a divinyl (hetero) aromatic compound, and a diisopropenyl (hetero)aromatic compound. In other embodiments, a polyfunctional monomer can have one or more amine, thiol, sulfide, alkynylly unsaturated, nitrone and/or nitroso, aldehyde, ketone, thiirane, ethylenically unsaturated, and/or epoxide moieties moieties; and one or more amine, thiol, sulfide, alkynylly unsaturated, nitrone and/or nitroso, aldehyde, ketone, thiirane, ethylenically unsaturated, and/or epoxide moieties, wherein the first and second moieties are different. A non-limiting example is a divinylbenzene monoxide.

The CHIP material can be made, for example, by polymerization of a molten mixture of chalcogenic monomers with the comonomers. Thus, in one aspect, the invention provides a method for making the CHIP material as described above. The method includes heating a mixture of the chalcogenic monomers and the one or more monomers together at a temperature sufficient to initiate polymerization (i.e., through free radical polymerization, through anionic polymerization, or through both, depending on the monomers used). For example, elemental sulfur, elemental selenium, selenium sulfide, or combinations thereof are polymerized with the comonomers. For example, in one embodiment, the method includes heating the mixture to a temperature in the range of about 120° C. to about 230° C., e.g., in the range of about 160° C. to about 230° C. The person of skill in the art will select conditions that provide the desired level of polymerization, in certain embodiments, the polymerization reaction is performed under ambient pressure. However, in other embodiments, the polymerization reaction can be performed at elevated pressure (e.g., in a bomb or an autoclave). Elevated pressures can be used to polymerize more volatile monomers, so that they do not vaporize under the elevated temperature reaction conditions.

In certain embodiments, it can be desirable to use a nucleophilic viscosity modifier in liquefying the chalcogenic monomers, for example, before adding one or more of the monomers (e.g., before adding any polyfunctional monomer). For example, in certain embodiments, the chalcogenic monomers is first heated with a viscosity modifier, then the viscosity-modified chalcogenic monomers are heated with one or more monomers (e.g., with one or more polyfunctional monomers). The nucleophilic viscosity modifier can be, for example, a phosphorus nucleophile (e.g., a phosphine), a sulfur nucleophile (e.g., a thiol) or an amine nucleophile (e.g., a primary or secondary amine). When the chalcogenic monomers are heated in the absence of a nucleophilic viscosity modifier, the chalcogenic monomer rings can open to form, e.g., diradicals, which can combine to form linear chains which can provide a relatively high overall viscosity to the molten material. Nucleophilic viscosity modifiers can break these linear chains into shorter lengths, thereby lowering the overall viscosity of the molten material and making the chalcogenic monomer mixture easier to mix with other species and to stir for efficient processing. Some of the nucleophilic viscosity modifier will react to be retained as a covalently bound part of the polymer, and some will react to form separate molecular species, with the relative amounts depending on nucleophile identity and reaction conditions. While some of the nucleophilic viscosity modifier may end up as a separate molecular species from the polymer chain, as used herein, nucleophilic viscosity modifiers may become part of the polymer. Non-limiting examples of nucleophilic viscosity modifiers include triphenylphosphine, aniline, benzenethiol, and N,N-dimethylaminopyridine. Nucleophilic viscosity modifiers can be used, for example, in an amount up to about 10 wt %, or even up to about 5 wt % of the CHIP material. When a nucleophilic viscosity modifier is used, in certain embodiments it can be used in the range of about 5 wt % to about 15 wt % of the CHIP material.

In certain embodiments, a monofunctional monomer can be used to reduce the viscosity of the CHIP material, for example, before adding other monomers (e.g., before adding any polyfunctional monomer). For example, in certain embodiments, the CHIP material is first heated with one or more monofunctional monomers. While not intending to be bound by theory, the inventors surmise that inclusion of monofunctional monomers into the polymer chains disrupts intermolecular associations and thus decreases the viscosity. The monofunctional monomer can be, for example, a mono(meth)acrylate such as benzyl methacrylate, a mono(oxirane) such as a styrene oxide or a glycidyl phenyl ether, or a mono(thiirane) such as t-butyl thiirane or phenoxymethylthiirane. A monofunctional monomer can be used to modify the viscosity of the CHIP material, for example, in an amount up to about 10 wt %, up to about 5 wt %, or even up to about 2 wt % of the CHIP material. When a monofunctional monomer is used to modify the viscosity of the CHIP material, in certain embodiments, it can be used in the range of about 0.5 wt % to about 5 wt %, or even about 0.5 wt % to about 3 wt % of the CHIP material.

Of course, viscosity modification is not required, so in other embodiments the chalcogenic monomers are heated together with the one or more monomers (and particularly with one or more polyfunctional monomers) without viscosity modification. In other embodiments, a solvent, e.g., a halobenzene such as 1,2,4-trichlorobenzene, a benzyl ether, or a phenyl ether, can be used to modify the viscosity of the materials for ease of handling. The solvent can be added, for example, to the chalcogenic monomers before reaction with a monomer in order to reduce its viscosity, or to the polymerized material in order to aid in processing into a desired form factor. A decrease in viscosity at elevated temperatures (e.g., >about 140° C.) can allow sufficient flow.

A further aspect of the invention pertains to a photonic crystal comprising at least one layer of a first polymer having a high refractive index, and at least one layer of a second polymer having a low refractive index, wherein the layer of the second polymer is disposed over or below the layer of the first polymer, wherein the first polymer comprises a chalcogenic hybrid inorganic/organic polymer (CHIP) material comprising:
    a. one or more chalcogenic monomers at a level of at least 50 wt % of the CHIP material; and
    b. one or more comonomers each selected from a group consisting of amine comonomers, thiol comonomers, sulfide comonomers, alkynylly unsaturated comonomers, epoxide comonomers, nitrone comonomers, aldehyde comonomers, ketone comonomers, thiirane comonomers, ethylenically unsaturated comonomers, styrenic comonomers, vinylic comonomers, methacrylate comonomers, acrylonitrile comonomers, allylic monomers, acrylate monomers, vinylpyridine monomers, isobutylene monomers, maleimide monomers, norbornene monomers, monomers having at least one vinyl ether moiety, and monomers having at least one isopropenyl moiety, at a level in the range of about 5-50 wt % of the CHIP material.

In some embodiments, the photonic crystal reflects at least one bandwidth in a short-wave infrared to mid-infrared spectrum.

In some embodiments, the photonic crystal comprises a first polymer layer, wherein a thickness of the first polymer layer is about 1-5000 nm. Furthermore, the thickness of the first polymer layer may be about 200-800 nm.

In some embodiments, the photonic crystal comprises a second polymer layer, wherein a thickness of the second polymer layer is about 1-5000 nm. Furthermore, the thickness of the second polymer layer may be about 200-800 nm.

The photonic crystal or other derived device of the invention may further comprise a plurality of alternating layers of the first polymer and the second polymer.

The photonic crystal, or other derived device of the invention may include a number of alternating layers wherein the number of alternating layers ranges from about 2-100.

In some embodiments, the second polymer is cellulose acetate or poly(vinyl alcohol) and may also include third, or multiple polymers, or materials to create alternative third, or disparate layers to modulate reflectivity.

In some embodiments, the chalcogenic monomers are selected from a group consisting of elemental sulfur, a liquid polysulfide, an oligomer containing sulfur, and an oligomer containing sulfur and selenium units.

In some embodiments, the chalcogenic monomers comprises sulfur monomers derived from elemental sulfur, and elemental selenium ($Se_8$).

In some embodiments, the first polymer has a high refractive index of at least about 1.6.

In some embodiments, the second polymer has a low refractive index of about 1.4-1.6.

In some embodiments, the CHIP material further comprises one or more termonomers selected from a group consisting of a vinyl monomer, an isopropenyl monomer, an acryl monomer, a methacryl monomer, an unsaturated hydrocarbon monomer, an epoxide monomer, a thiirane monomer, an alkynyl monomer, a diene monomer, a butadiene monomer, an isoprene monomer, a norbornene monomer, an amine monomer, a thiol monomer, a sulfide monomer, an alkynylly unsaturated monomer, a nitrone monomer, an aldehyde monomer, a ketone monomer, an ethylenically unsaturated monomer, and a styrenic monomer.

In some embodiments, the CHIP material further comprises one or more polyfunctional monomers selected from a group consisting of a polyvinyl monomer, a polyisopropenyl monomer, a polyacryl monomer, a polymethacryl monomer, a polyunsaturated hydrocarbon monomer, a polyepoxide monomer, a polythiirane monomer, a polyalkynyl monomer, a polydiene monomer, a polybutadiene monomer, a polyisoprene monomer, a polynorbornene monomer, a polyamine monomer, a polythiol monomer, a polysulfide monomer, a polyalkynylly unsaturated monomer, a polynitrone monomer, a polyaldehyde monomer, a polyketone monomer, and a polyethylenically unsaturated monomer.

Another aspect of the invention pertains to a photonic crystal device comprising a plurality of alternating layers of a first polymer having a high refractive index and a second polymer having a low refractive index, wherein the first polymer comprises a chalcogenic hybrid inorganic/organic polymer (CHIP) material comprising:
one or more chalcogenic monomers at a level of at least 50 wt % of the CHIP material; and
one or more comonomers each selected from a group consisting of amine comonomers, thiol comonomers, sulfide comonomers, alkynylly unsaturated comonomers, epoxide comonomers, nitrone comonomers, aldehyde comonomers, ketone comonomers, thiirane comonomers, ethylenically unsaturated comonomers, styrenic comonomers, vinylic comonomers, methacrylate comonomers, acrylonitrile comonomers, allylic monomers, acrylate monomers, vinylpyridine monomers, isobutylene monomers, maleimide monomers, norbornene monomers, monomers having at least one vinyl ether moiety, and monomers having at least one isopropenyl moiety, at a level in the range of about 5-50 wt % of the CHIP material.

In some embodiments, the plurality of alternating layers reflect at least one band in a short-wave infrared to mid-infrared spectrum.

In further embodiments, the photonic crystal device is a Bragg reflector, a dielectric mirror, a narrowband filter, a notch filter, a broadband filter, a spike filter, a R refractive coating, a IR reflective paint for heat management application, a reflective coating for the infrared (IR), or a Fabry-Perot etalon.

In further embodiments, the thickness of each alternating layer ranges from about 1-5000 nm. The thickness of each alternating layer may range from about 200-800 nm.

In further embodiments, the number of the alternating layers ranges from about 2 to 100 layers.

In some embodiments, the second polymer is cellulose acetate or poly(vinyl alcohol).

In some embodiments, the chalcogenic monomers are selected from a group consisting of elemental sulfur, a liquid polysulfide, an oligomer containing sulfur, and an oligomer containing sulfur and selenium units. Furthermore, the chalcogenic monomers may comprise sulfur monomers derived from elemental sulfur, and elemental selenium (Se8).

In some embodiments, the first polymer has a high refractive index of at least about 1.6.

In some embodiments, the second polymer has a low refractive index of about 1.4-1.6.

In some embodiments, the CHIP material further comprises one or more termonomers selected from a group consisting of a vinyl monomer, an isopropenyl monomer, an acryl monomer, a methacryl monomer, an unsaturated hydrocarbon monomer, an epoxide monomer, a thiirane monomer, an alkynyl monomer, a diene monomer, a butadiene monomer, an isoprene monomer, a norbornene monomer, an amine monomer, a thiol monomer, a sulfide monomer, an alkynylly unsaturated monomer, a nitrone monomer, an aldehyde monomer, a ketone monomer, an ethylenically unsaturated monomer, and a styrenic monomer.

In some embodiments, wherein the CHIP material further comprises one or more polyfunctional monomers selected from a group consisting of a polyvinyl monomer, a polyisopropenyl monomer, a polyacryl monomer, a polymethacryl monomer, a polyunsaturated hydrocarbon monomer, a polyepoxide monomer, a polythiirane monomer, a polyalkynyl monomer, a polydiene monomer, a polybutadiene monomer, a polyisoprene monomer, a polynorbornene monomer, a polyamine monomer, a polythiol monomer, a polysulfide monomer, a polyalkynylly unsaturated monomer, a polynitrone monomer, a polyaldehyde monomer, a polyketone monomer, and a polyethylenically unsaturated monomer.

Another aspect of the invention pertains to a method of fabricating a photonic crystal device comprising:
a. providing a substrate having a surface layer;
b. preparing a chalcogenic hybrid inorganic/organic polymer (CHIP) material, comprising:
 i. providing at least about 50 wt % of one or more chalcogenic monomers;
 ii. adding about 5-50 wt % of one or more comonomers to the chalcogenic monomers, wherein the one or more comonomers are selected from a group consisting of amine comonomers, thiol comonomers, sulfide comonomers, alkynylly unsaturated comonomers, epoxide comonomers, nitrone comonomers, aldehyde comonomers, ketone comonomers, thiirane comonomers, ethylenically unsaturated comonomers, styrenic comonomers, vinylic comonomers, methacrylate comonomers, acrylonitrile comonomers, allylic monomers, acrylate monomers, vinylpyridine monomers, isobutylene monomers, maleimide monomers, norbornene monomers, monomers having at least one vinyl ether moiety, and monomers having at least one isopropenyl moiety; and
 iii. polymerizing the comonomers with the chalcogenic monomers to form the CHIP material;
c. dissolving the CHIP material in a first solvent to form a first polymeric solution;
d. providing a low refractive index polymer;
e. dissolving the low refractive index polymer in a second solvent to form a second polymeric solution, wherein the second solvent is orthogonal to the first solvent such that the CHIP material is insoluble in the second solvent and the low refractive index polymer is insoluble in the first solvent; and
f. spin-coating a plurality of alternating layers of the first polymeric solution and the second polymeric solution on the surface layer of the substrate until a specified number of layers is disposed on the substrate.

In some embodiments, the plurality of alternating layers reflects at least one bandwidth in a short-wave infrared to mid-infrared spectrum.

In further embodiments, the method of fabricating a photonic crystal device comprises a photonic crystal device, wherein the photonic crystal device is a Bragg reflector, a dielectric mirror, a narrowband filter, a notch filter, a broadband filter, a spike filter, a IR refractive coating, a IR reflective paint for heat management applications, a reflective coating for the infrared (IR), or a Fabry-Perot etalon.

In some embodiments, wherein the thickness of each alternating layer ranges from about 1-5000 nm. Furthermore, the thickness of each alternating layer may range from about 200-800 nm.

In some embodiments, the low refractive index polymer is cellulose acetate or poly(vinyl alcohol).

In some embodiments, the chalcogenic monomers are selected from a group consisting of elemental sulfur, a liquid polysulfide, an oligomer containing sulfur, and an oligomer containing sulfur and selenium units. Further, the chalcogenic monomers may comprise sulfur monomers derived from elemental sulfur, and elemental selenium ($Se_8$, or other allotropes).

In some embodiments, the first solvent is an organic solvent.

In some embodiments, wherein the first solvent is halobenzene.

In some embodiments, wherein the second solvent is an aqueous or organic solvent. The second solvent may be water.

In some embodiments, the CHIP material has a high refractive index of at least about 1.6.

In some embodiments, wherein the low refractive index polymer has a low refractive index of about 1.4-1.6.

In some embodiments, the number of layers ranges from about 10 to 100 layers.

In some embodiments, the method of fabricating a photonic crystal device involves preparing the CHIP material further comprises polymerizing the CHIP material with one or more termonomers selected from a group consisting of a vinyl monomer, an isopropenyl monomer, an acryl monomer, a methacryl monomer, an unsaturated hydrocarbon monomer, an epoxide monomer, a thiirane monomer, an alkynyl monomer, a diene monomer, a butadiene monomer, an isoprene monomer, a norbornene monomer, an amine monomer, a thiol monomer, a sulfide monomer, an alkynylly unsaturated monomer, a nitrone monomer, an aldehyde monomer, a ketone monomer, an ethylenically unsaturated monomer, and a styrenic monomer.

In further embodiments, wherein preparing the CHIP material further comprises polymerizing the CHIP material with one or more polyfunctional monomers selected from a group consisting of a polyvinyl monomer, a polyisopropenyl monomer, a polyacryl monomer, a polymethacryl monomer, a polyunsaturated hydrocarbon monomer, a polyepoxide monomer, a polythiirane monomer, a polyalkynyl monomer, a polydiene monomer, a polybutadiene monomer, a polyisoprene monomer, a polynorbornene monomer, a polyamine monomer, a polythiol monomer, a polysulfide monomer, a polyalkynylly unsaturated monomer, a polynitrone monomer, a polyaldehyde monomer, a polyketone monomer, and a polyethylenically unsaturated.

A further aspect of the invention involves a method of fabricating a photonic crystal device, comprising:
 a. preparing a chalcogenic hybrid inorganic/organic polymer (CHIP) material, comprising:
  i. providing at least about 50 wt % of one or more chalcogenic monomers;
  ii. adding about 5-50 wt % of one or more comonomers to the chalcogenic monomers, wherein the one or more comonomers are selected from a group consisting of amine comonomers, thiol comonomers, sulfide comonomers, alkynylly unsaturated comonomers, epoxide comonomers, nitrone comonomers, aldehyde comonomers, ketone comonomers, thirane comonomers, ethylenically unsaturated comonomers, styrenic comonomers, vinylic comonomers, methacrylate comonomers, acrylonitrile comonomers, allylic monomers, acrylate monomers, vinylpyridine monomers, isobutylene monomers, maleimide monomers, norbornene monomers, monomers having at least one vinyl ether moiety, and monomers having at least one isopropenyl moiety; and
  iii. polymerizing the comonomers with the chalcogenic monomers to form the CHIP material;
 b. melting the CHIP material to form a first polymeric melt solution;
 c. melting a low refractive index polymer to form a second polymeric melt solution; and
 d. performing a multilayered co-extrusion technique utilizing the first polymeric melt solution and the second polymeric melt solution to produce the photonic crystal device comprising a plurality of alternating layers of the CHIP material and the low refractive index polymer.

In some embodiments, the plurality of alternating layers reflect at least one bandwidth in a short-wave infrared to mid-infrared spectrum.

In some embodiments, the photonic crystal device is a Bragg reflector, a dielectric mirror, a narrowband filter, a notch filter, a broadband filter, a spike filter, a IR refractive coating, a IR reflective paint for heat management applications, a reflective coating for the infrared (IR), or a Fabry-Perot etalon.

In some embodiments, the thickness of each alternating layer ranges from about 1-5000 nm. The thickness of each alternating layer may range from about 200-800 nm.

Furthermore, the number of layers may range from about 10 to 100 layers.

In further embodiments, the low refractive index polymer is cellulose acetate or poly(vinyl alcohol).

In further embodiments, the chalcogenic monomers are selected from a group consisting of elemental sulfur, a liquid polysulfide, an oligomer containing sulfur, and an oligomer containing sulfur and selenium units. Further, the chalcogenic monomers may comprise sulfur monomers derived from elemental sulfur, and elemental selenium (Se8).

In some embodiments, the CHIP material has a high refractive index of at least about 1.6.

In some embodiments, the low refractive index polymer has a low refractive index of about 1.4-1.6.

In some embodiments, the preparation of the CHIP material further comprises polymerizing the CHIP material with one or more termonomers selected from a group consisting of a vinyl monomer, an isopropenyl monomer, an acryl monomer, a methacryl monomer, an unsaturated hydrocarbon monomer, an epoxide monomer, a thiirane monomer, an alkynyl monomer, a diene monomer, a butadiene monomer, an isoprene monomer, a norbornene monomer, an amine monomer, a thiol monomer, a sulfide monomer, an alkynylly unsaturated monomer, a nitrone monomer, an aldehyde monomer, a ketone monomer, an ethylenically unsaturated monomer, and a styrenic monomer.

In some embodiments, the preparation of the CHIP material further comprises polymerizing the CHIP material with one or more polyfunctional monomers selected from a group consisting of a polyvinyl monomer, a polyisopropenyl monomer, a polyacryl monomer, a polymethacryl monomer, a polyunsaturated hydrocarbon monomer, a polyepoxide monomer, a polythiirane monomer, a polyalkynyl monomer, a polydiene monomer, a polybutadiene monomer, a polyisoprene monomer, a polynorbornene monomer, a polyamine monomer, a polythiol monomer, a polysulfide monomer, a polyalkynylly unsaturated monomer, a polynitrone monomer, a polyaldehyde monomer, a polyketone monomer, and a polyethylenically unsaturated.

A further aspect of the invention pertains to a method of fabricating a photonic crystal device comprising providing a surface layer; and depositing a plurality of alternating layers of a first polymer and a second polymer on said surface layer; wherein the first polymer has a high refractive index, wherein the second polymer has a low refractive index, wherein the first polymer comprises a chalcogenic hybrid inorganic/organic polymer (CHIP) material comprising:
  a. one or more chalcogenic monomers at a level of at least 50 wt % of the CHIP material; and
  b. one or more comonomers each selected from a group consisting of amine comonomers, thiol comonomers, sulfide comonomers, alkynylly unsaturated comonomers, epoxide comonomers, nitrone comonomers, aldehyde comonomers, ketone comonomers, thiirane comonomers, ethylenically unsaturated comonomers, styrenic comonomers, vinylic comonomers, methacrylate comonomers, acrylonitrile comonomers, allylic monomers, acrylate monomers, vinylpyridine monomers, isobutylene monomers, maleimide monomers, norbornene monomers, monomers having at least one vinyl ether moiety, and monomers having at least one isopropenyl moiety, at a level in the range of about 5-50 wt % of the CHIP material.

In some embodiments, the plurality of alternating layers reflect at least one bandwidth in a short-wave infrared to mid-infrared spectrum.

In some embodiments, the photonic crystal device is a Bragg reflector, a dielectric mirror, a narrowband filter, a notch filter, a broadband filter, a spike filter, a IR refractive coating, a IR reflective paint for heat management applications, a reflective coating for the infrared (IR), or a Fabry-Perot etalon.

In some embodiments, the thickness of each alternating layer ranges from about 1-5000 nm. Further, the thickness of each alternating layer may range from about 200-800 nm.

In some embodiments, the plurality of alternating layers ranges from about 10 to 100 layers.

In some embodiments, the second polymer is cellulose acetate or poly(vinyl alcohol) and may also include third, or multiple polymers, or materials to create alternative third, or disparate layers to modulate reflectivity.

In some embodiments, the chalcogenic monomers are selected from a group consisting of elemental sulfur, a liquid polysulfide, an oligomer containing sulfur, and an oligomer containing sulfur and selenium units.

In some embodiments, the chalcogenic monomers comprises sulfur monomers derived from elemental sulfur, and elemental selenium ($Se_8$, or other allotropes).

In some embodiments, the first polymer has a high refractive index of at least about 1.6.

In some embodiments, the second polymer has a low refractive index of about 1.4-1.6.

In some embodiments, the CHIP material further comprises one or more termonomers selected from a group consisting of a vinyl monomer, an isopropenyl monomer, an acryl monomer, a methacryl monomer, an unsaturated hydrocarbon monomer, an epoxide monomer, a thiirane monomer, an alkynyl monomer, a diene monomer, a butadiene monomer, an isoprene monomer, a norbornene monomer, an amine monomer, a thiol monomer, a sulfide monomer, an alkynylly unsaturated monomer, a nitrone monomer, an aldehyde monomer, a ketone monomer, an ethylenically unsaturated monomer, and a styrenic monomer.

In further embodiments, the CHIP material further comprises one or more polyfunctional monomers selected from a group consisting of a polyvinyl monomer, a polyisopropenyl monomer, a polyacryl monomer, a polymethacryl monomer, a polyunsaturated hydrocarbon monomer, a polyepoxide monomer, a polythiirane monomer, a polyalkynyl monomer, a polydiene monomer, a polybutadiene monomer, a polyisoprene monomer, a polynorbornene monomer, a polyamine monomer, a polythiol monomer, a polysulfide monomer, a polyalkynylly unsaturated monomer, a polynitrone monomer, a polyaldehyde monomer, a polyketone monomer, and a polyethylenically unsaturated monomer.

EXAMPLES

The following are non-limiting examples of the present invention. The Sty-S-BOC monomer was synthesized via lithiation of 4-bromostyrene, followed by thiylation of the lithiated monomer with elemental sulfur and trapping of the thiylate with t-BOC anhydride (50% yield). Free radical polymerization methods are then used to create polymers from this monomer and post-processing of thin films is employed to create high refractive polymer domains. Equivalents or substitutes are within the scope of the invention.

Example 1: St-S-BOC Monomer Synthesis

As shown in Scheme 2, a flame dried 3 necked round bottomed flask was equipped with a magnetic stir bar and charged with 25 mL THF and 25 mL hexanes then cooled to −78° C. and bromostyrene was added (2.02 g, 11 mmol) under argon, nBuLi (1.6 M in hexanes) (6.8 mL, 11 mmol) was added dropwise and stirred 1.5 hr followed by the addition of recrystallized elemental sulfur (352 mg, 11 mmol on S atom basis) added at −78° C. then warmed to −20° C. and stirred for 30 minutes. BoC-anhydride (4.8 g, 22.0 mmol) was added at −20° C. and then stirred at this temperature for 2 hours. The reaction was quenched by pouring water into the reaction immediately after removing the reaction vessel from the cooling bath. The mixture was extracted with diethyl ether twice then washed with water 1× and brine 1×, dried, filtered, and concentrate down under reduced pressure. The residual BoC-anhydride was removed by sublimation at 60° C. for 1.5 hours. The residue was purified by $SiO_2$ column chromatography first in 7.5% EtOAc in hexanes then again in 2% EtOAc in hexanes.

The resulting pale yellow oil was concentrated down under reduced pressure.

Scheme 2.

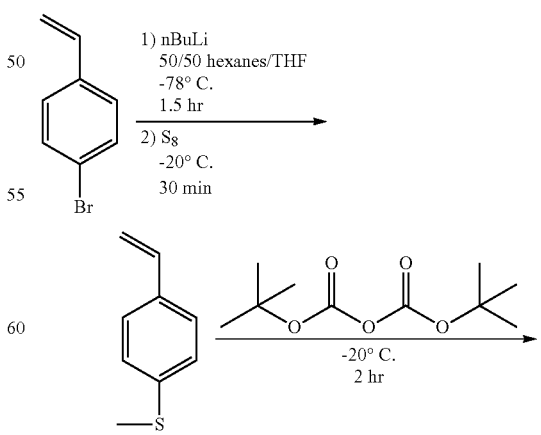

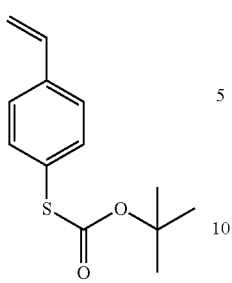

Example 2: Poly(St-S-BOC) Synthesis

Referring to Scheme 3, a vial was loaded with a magnetic stir bar and charged with St-S-BOC monomer (200 mg, 0.85 mmol) along with AIBN (13.5 mg, 0.082 mmol) and dissolved in THF (0.1 mL). The solution was sparged with argon for 15 minutes then placed in a 60° C. oil bath and stirred at this temperature for 1.75 hrs. The solution was dissolved in DCM and precipitated with hexanes.

Scheme 3.

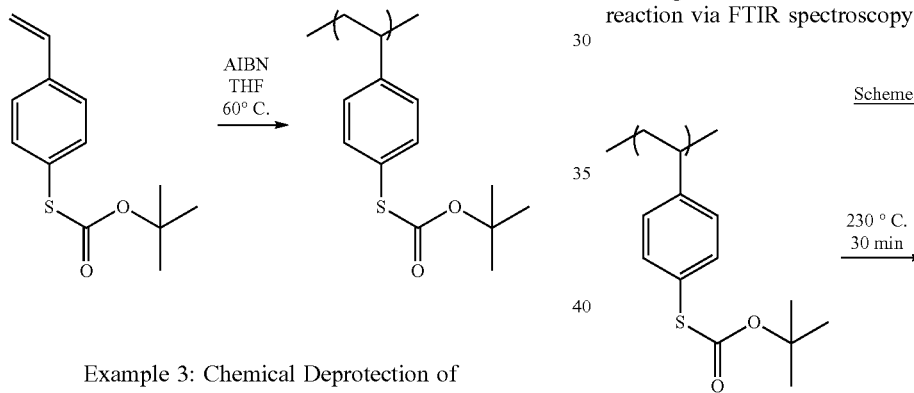

Example 3: Chemical Deprotection of Poly(St-S-BOC)

As shown in Scheme 4, a vial was loaded with a magnetic stir bar and charged with p(St-S-BOC) (60 mg, 2.1×10$^{-6}$ mol) and dissolved in 0.5 mL of THF. TFA (1.0 mL, 13.0 mmol) was then added. The reaction mixture formed a gel in solution after ~10 minutes.

Scheme 4.

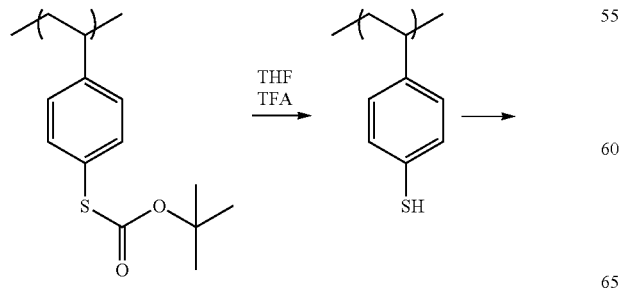

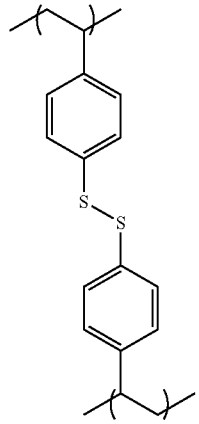

Example 4: Thermal Deprotection of Poly(St-S-BOC) as a Thin Film

Figure 4:
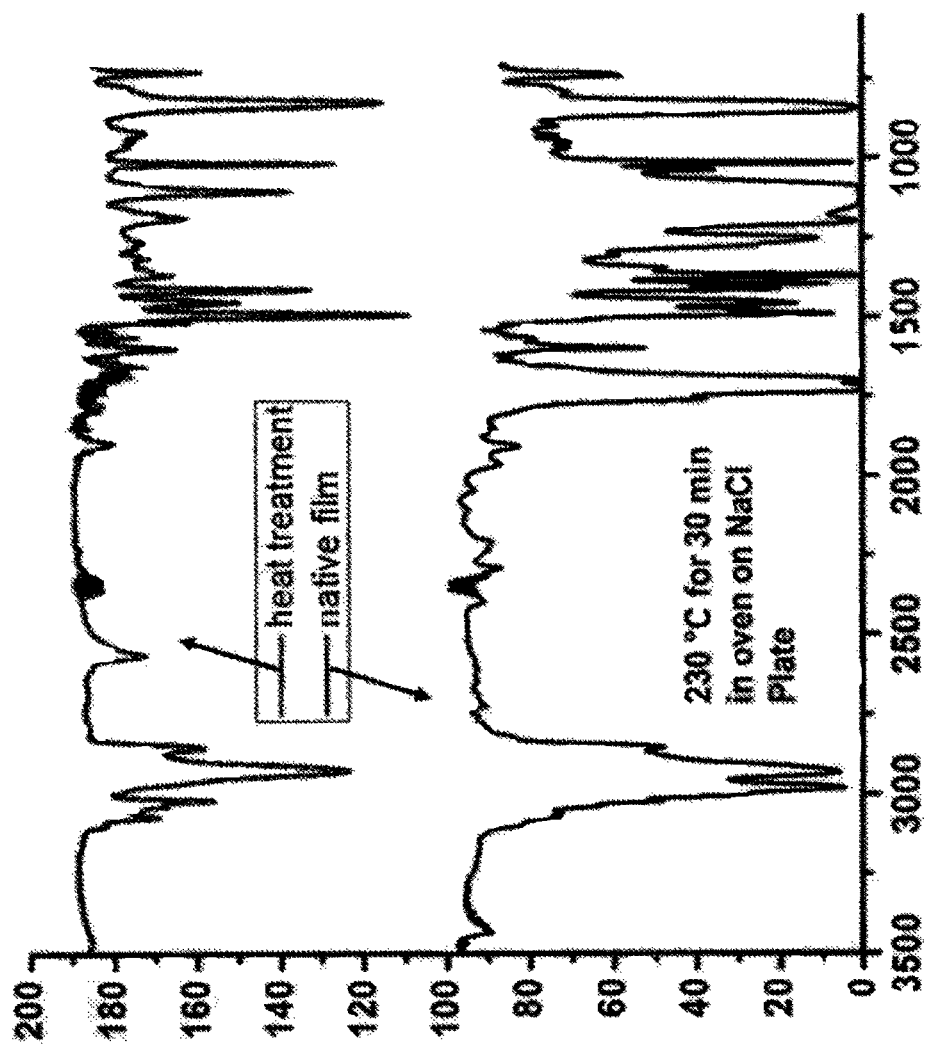
FIG. 4 shows an FTIR spectra for the thermal deprotection of poly(St-S-BOC) to produce of poly(St-disulfide).

If Referring to Scheme 5, approximately 8 μm film of p(St-S-BoC) was spin coated onto a glass substrate, which were then placed in a 230° C. oven for 30 minutes. These thermal deprotection conditions were determined by performing the reaction on NaCl plates and monitoring the reaction via FTIR spectroscopy (FIG. 4).

Scheme 5.

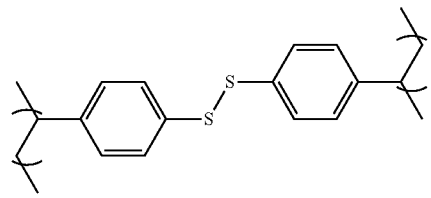

Example 5: Photochemical Deprotection of Poly(St-S-BOC) as a Thin Film

Figure 5A:
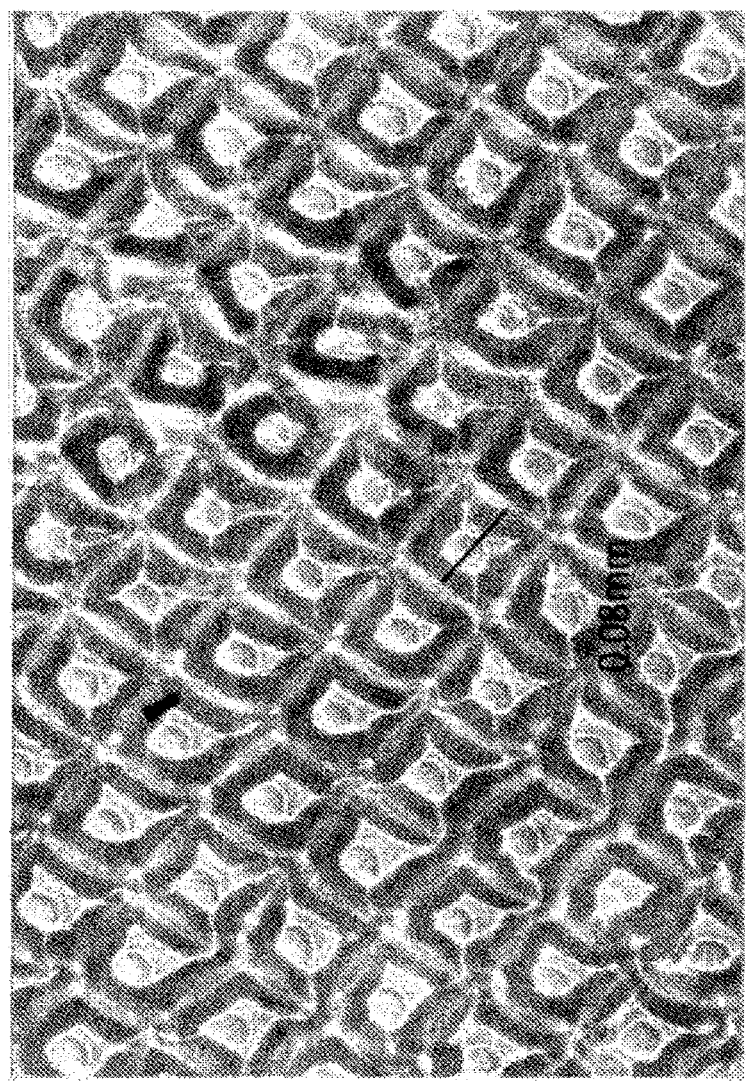
FIGS. 5A and 5B show an exemplary embodiment of a poly(St-S-BOC) film spin coated onto a glass substrate and exposed to a 254 nm light source for 45 minutes with the TEM grid as a mask (FIG. 5B), and then developed in THF (FIG. 5A).
Figure 5B:
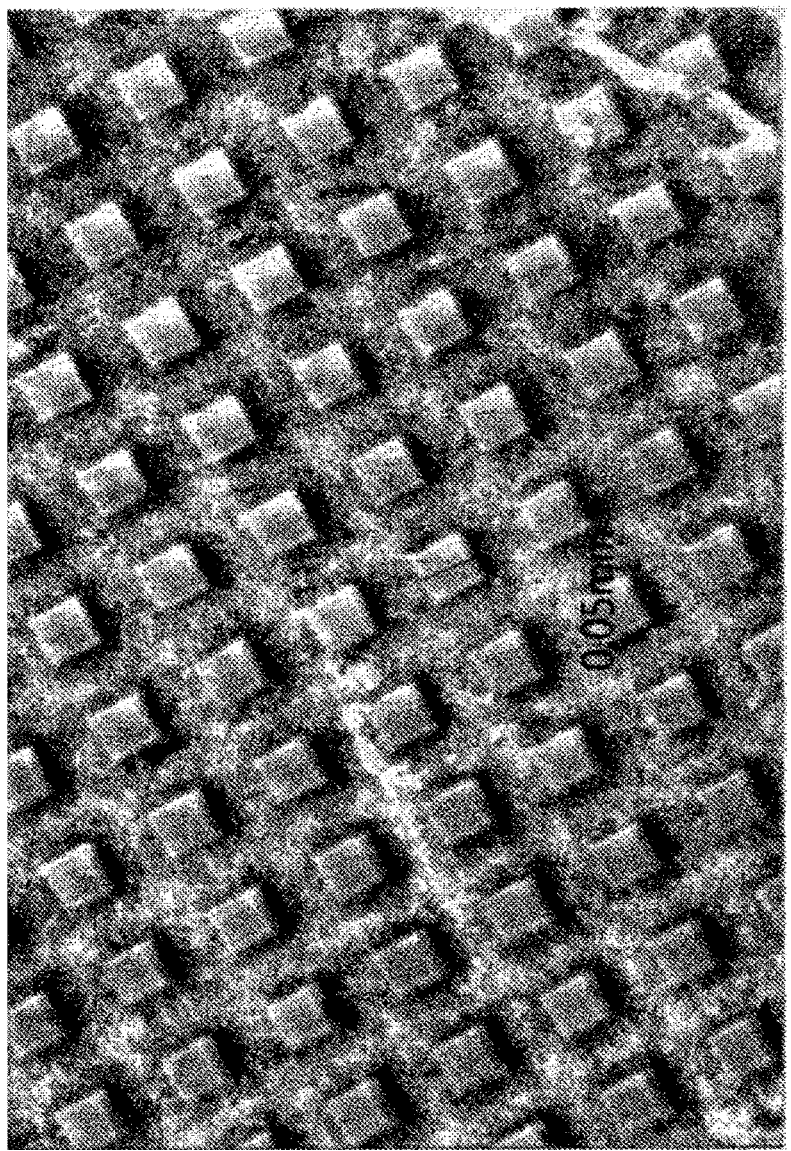

As shown in Scheme 6, approximately 300 nm films of p(St-S-BOC) were spin coated onto glass substrates containing 20% wt/wt (relative to the mass of polymer) of a PAG, (4-phenylthiophenyl)diphenylsulfonium triflate. Referring to FIGS. 5A and 5B, the film coated glass substrates were exposed to a 254 nm light source with a TEM grid as a mask for 45 minutes, and then developed in THF.

Scheme 6.

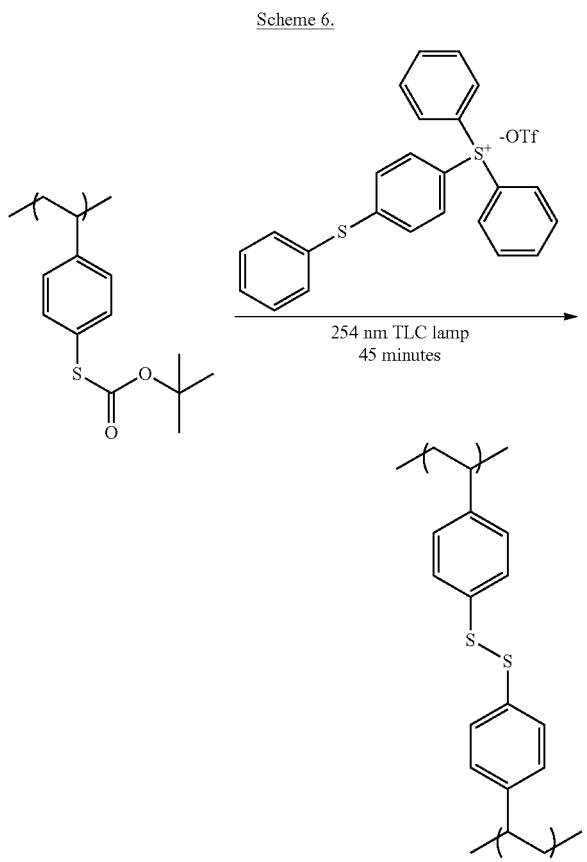

Example 6: Change in Refractive Index After Deprotection of p(St-S-BOC)

Figure 6:
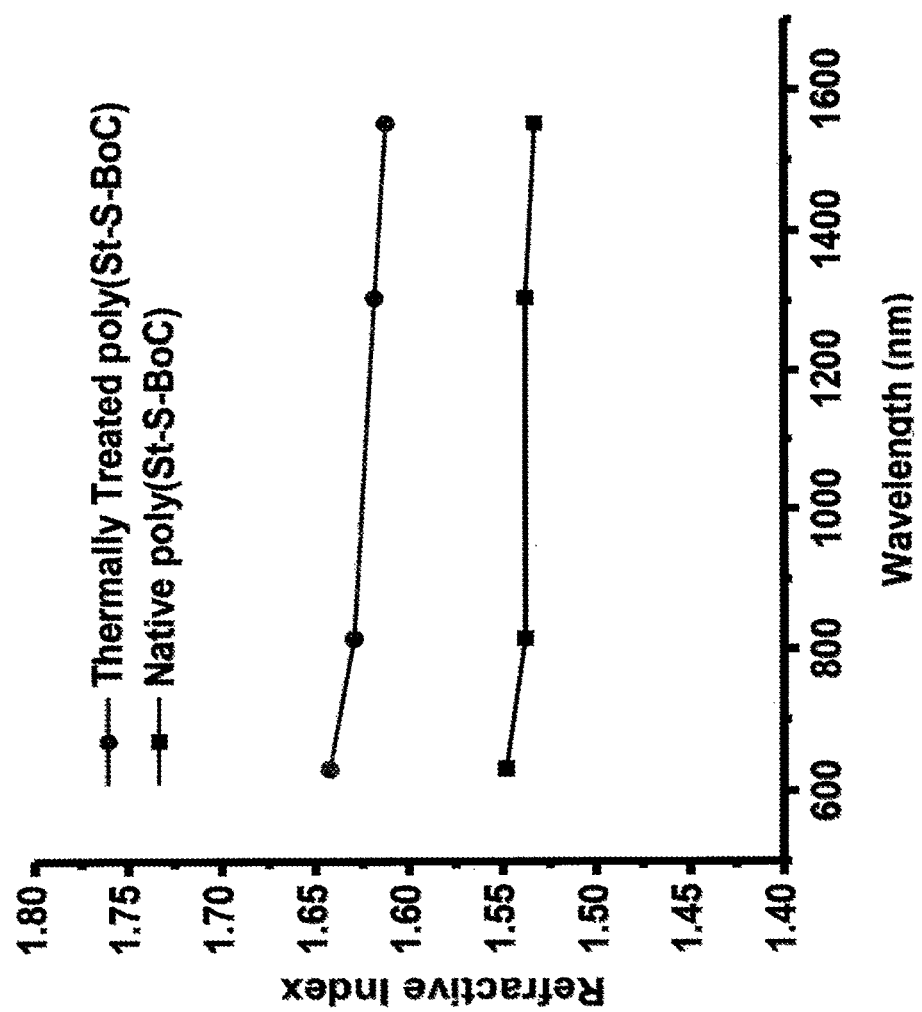
FIG. 6 shows the refractive indexes of a native poly(St-S-BOC) film and a thermally deprotected film of poly(St-S-BOC).
Figure 7:
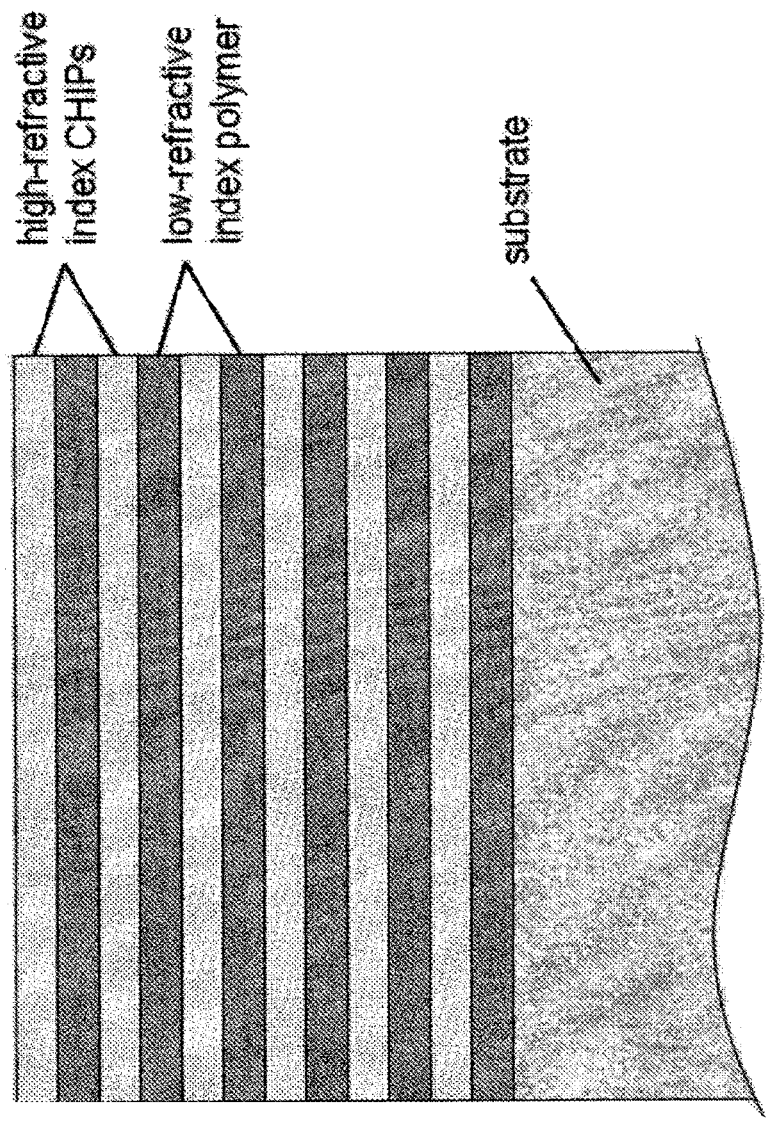
FIG. 7 shows an embodiment of a Bragg reflector of the present invention.
Figure 8:
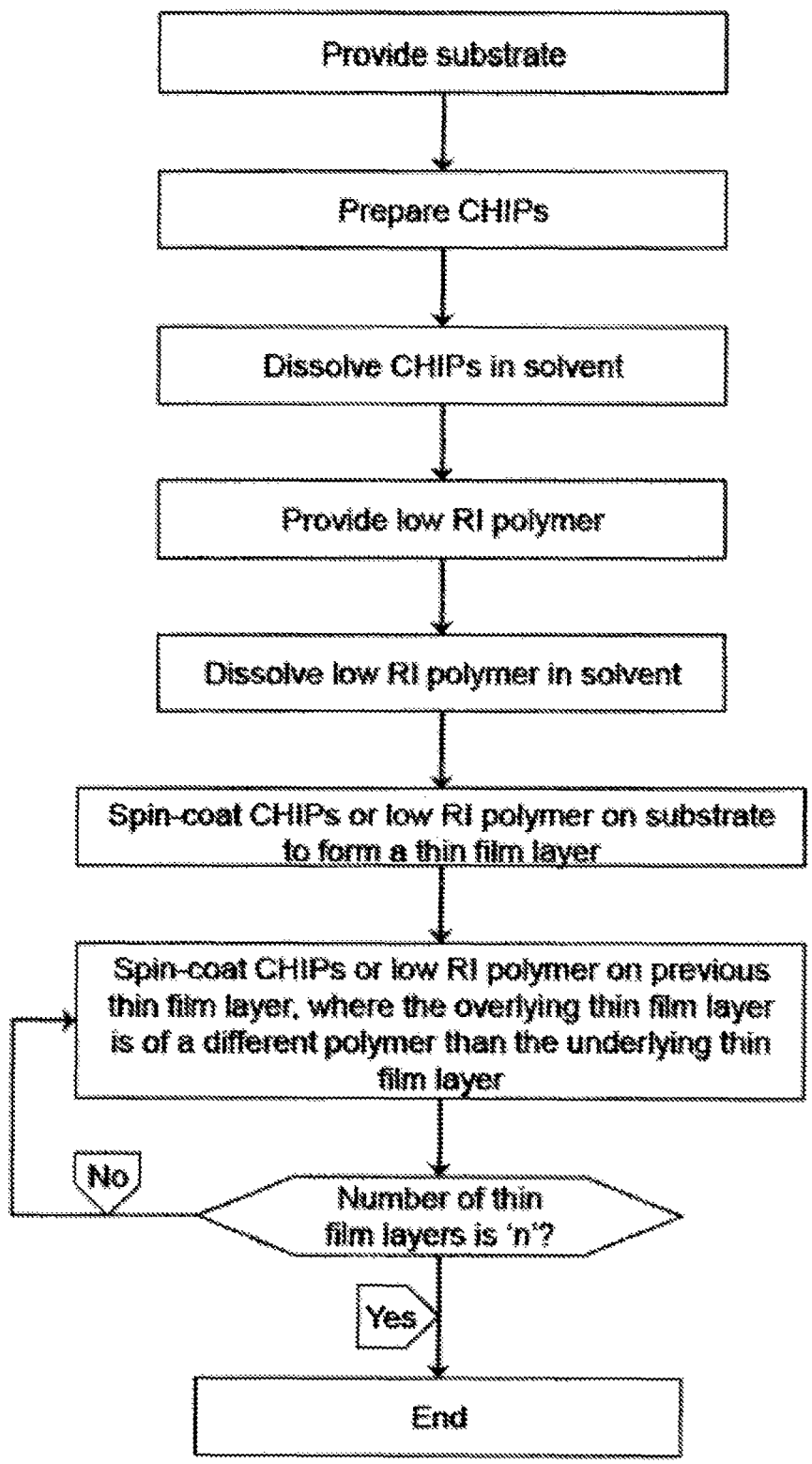
FIG. 8 shows a non-limiting schematic for fabricating the Bragg reflector.
Figure 9:
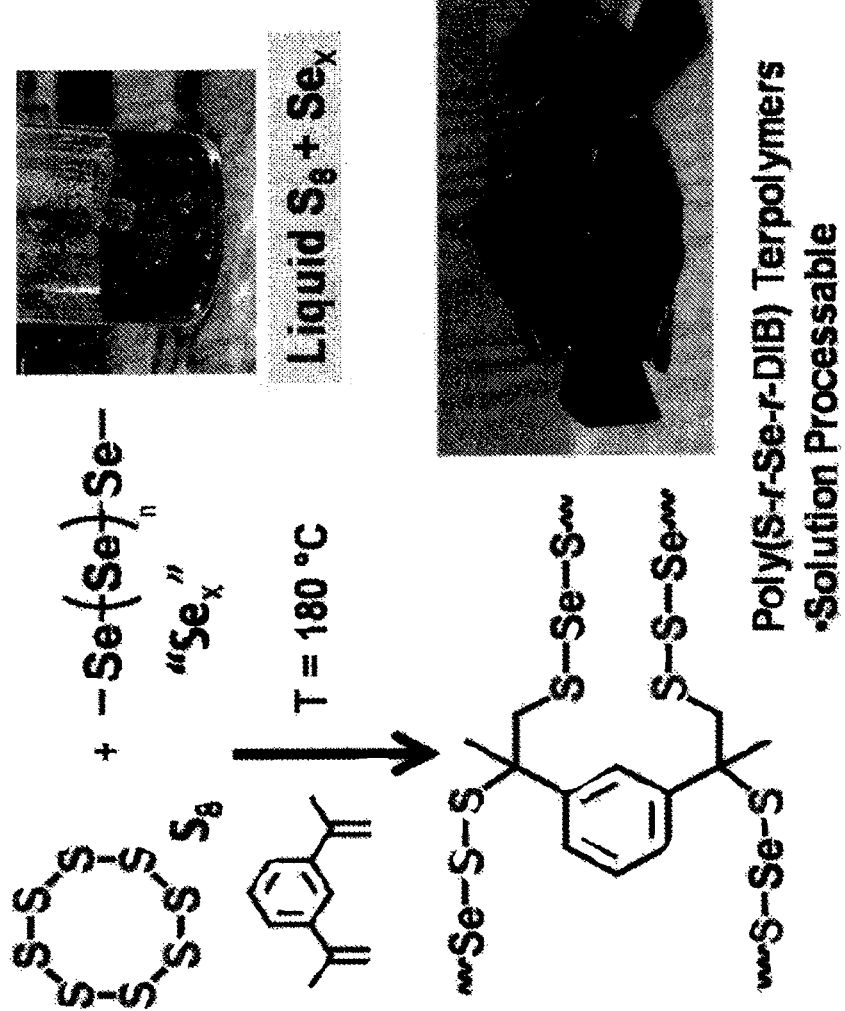
FIG. 9 shows a non-limiting reaction scheme for producing the CHIPs terpolymer.
Figure 10:
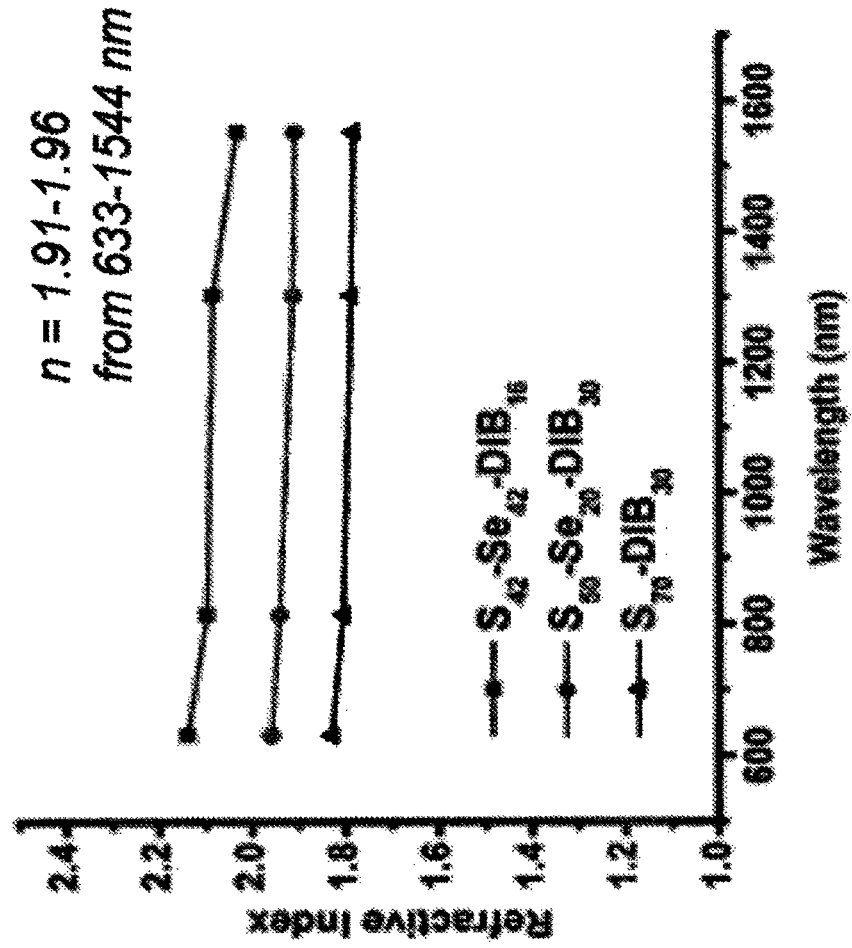
FIG. 10 shows a plot of refractive index vs. wavelength for the CHIPs terpolymers having varying compositions.
Figure 11:
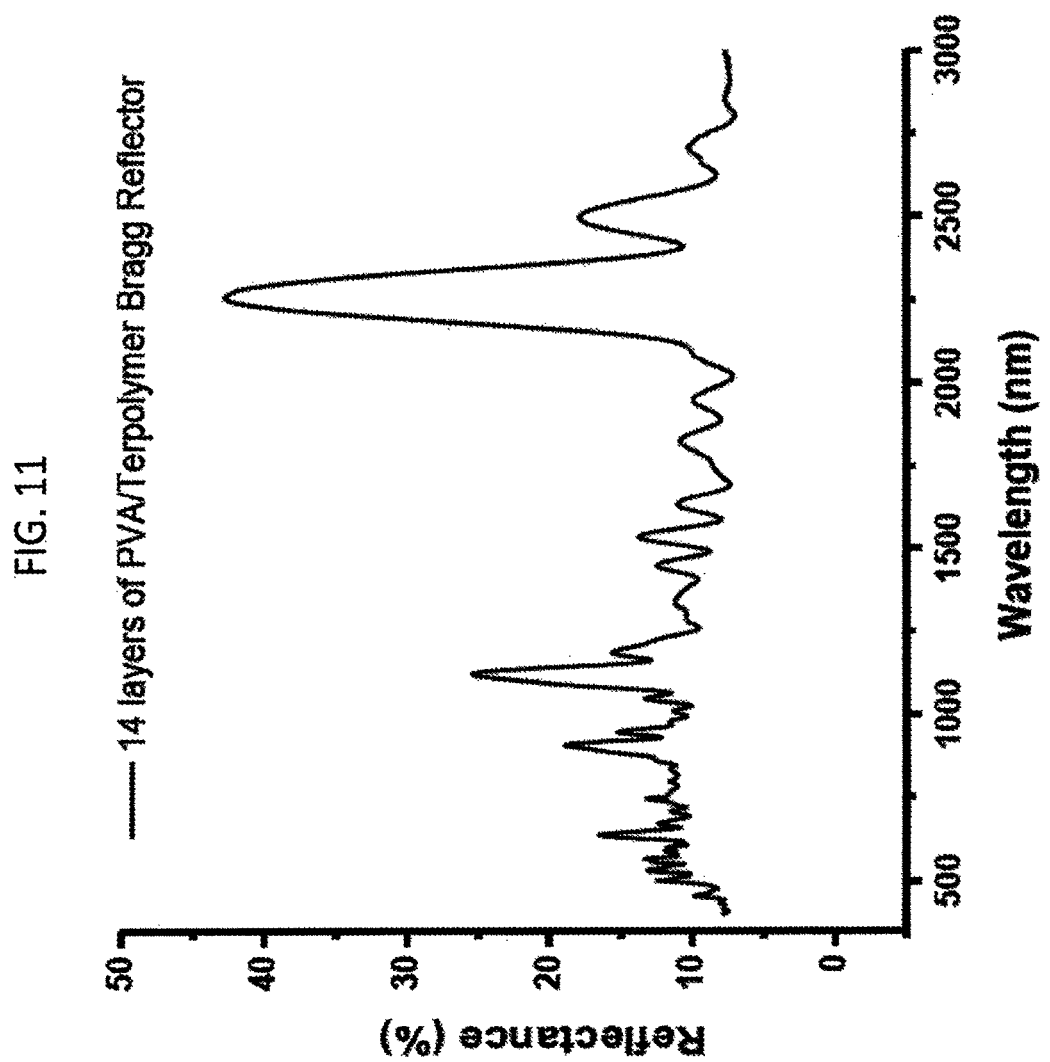
FIG. 11 shows a reflectance spectra for a 14-layer PVA/CHIPs Terpolymer Bragg Reflector of the present invention. Since the multilayer film is intended to reflect light at 2 μm, the spectra shows a high % reflectivity at this wavelength.

Approximately 8 μm film of p(St-S-BOC) was spin coated onto a glass substrate. Then the refractive index of the native film was measured by prism coupled ellipsometry. The film was then placed in a 230° C. oven for 30 minutes and the refractive index was measured for the deprotected film. The refractive index values of the native film and the deprotected film are shown in FIG. 6 and TABLE 1.

TABLE 1

| Wavelength (nm) | Refractive index (native film) | Refractive index (deprotected film) |
|---|---|---|
| 632 | 1.548 | 1.6428 |
| 816 | 1.538 | 1.6299 |
| 1305 | 1.538 | 1.6187 |
| 1554 | 1.533 | 1.61256 |

Example 7

Preparation of poly(sulfur-random-selenium-random-1,3-diisopropylbenzene) (poly(S-r-Se-r-DIB)) terpolymers To a 11 mL glass vial equipped with a magnetic stir bar was added sulfur (S8, 1.5 g, 46.78 mmol) and heated to T=160° C. in a thermostated oil bath until a clear orange colored molten phase was formed. The vial was then transferred to an adjacent T=150° C. in a thermostated oil bath where selenium (Se, 0.6 g, 7.59 mmol) was then directly added to the molten sulfur medium, 1,3-Diisopropenylbenzene (DIB, 0.9 g (0.97 mL)) was then directly added to the molten sulfur-selenium medium via syringe. The resulting mixture was stirred at T=150° C. for 1 to 1½ hours, which resulted in vitrification of the reaction media. The product was then taken directly from the vial using a metal spatula and removal of the magnetic stir bar for determination of yields after allowing the reaction mixture to cool to room temperature.

Spin Coating poly(S-r-Se-r-DIB) terpolymer Thin Films.

Solutions of terpolymer in chlorobenzene for spin coating were prepared by first saturating 1 mL of chlorobenzene with 250 mg of terpolymer at 135° C. This saturated solution was allowed to cool to room temperature then diluted to 30% of the saturated solution. This dilution was used to spin coat terpolymer films in the fabrication of Bragg reflectors. About 1 mL of solution was deposited onto a hot substrate (T=120° C) and spun for 59 seconds at 6 k RPM in static mode. The film when then dried on a preheated T=120° C. hot plate for 2 minutes.

Preparation of poly(vinyl alcohol) (PVA) in a Water Solution

A 50 mg/mL solution of PVA in water was prepared by dispersing high MW PVA in water then microwaving until dissolved.

Spin Coating poly(vinyl alcohol) Thin Films.

1.5 mL of solution was deposited onto a hot substrate (T=120° C.) and spun for 59 seconds at 6 k RPM in static mode. The film was then dried on a preheated hot plate (T=120° C.) for 5 minutes.

Wholly Polymeric CHIPs/PVA 2 μm Bragg Reflector.

A 2 μm Bragg reflector (also known as a dielectric mirror, of 1-D photonic crystal) is comprised of 12 alternating layers of a chalcogenide terpolymer and PVA. The chalcogenide terpolymer is poly(sulfur-random-selenium-(1,3-diisopropenyl-benzene) (poly(S-r-Se-r-DIB)) having 50-wt % S, 20-wt %, Se, 30-wt % DIB feed ratios. The refractive index (n) is 1.91-1.96 from 633-1554 nm. Each poly(S-r-Se-r-DIB) layer can have a film thickness=242 nm. The refractive index (n) is 1.46 and each layer can have a film thickness=333 nm. Each film layer is alternating spin coated. The poly(S-r-Se-DIB) is dissolved in chlorobenzene and the PVA is dissolved in water. The solvents must be "orthogonal" where the water-PVA solution cannot dissolve the underlying terpolymer and vice versa (i.e. the chlorobenzene-terpolymer does not dissolve PVA).

Wholly Polymeric CHIPs 4 μm Bragg Reflector.

A 4 μm Bragg reflector (also known as a dielectric mirror, of 1-D photonic crystal) is comprised of 12 alternating layers of a chalcogenide terpolymer and PVA. The chalcogenide terpolymer is poly(sulfur-random-selenium-(1,3-diisopropenyl-benzene) (poly(S-r-Se-r-DIB)) having 50-wt % S, 20-wt %, Se, 30-wt % DIB feed ratios. The refractive index (n) is 1.91-1.96 from 633-1554 nm. Each poly(S-r-Se-r-DIB) layer can have a film thickness=526 nm. The refractive index (n) is 1.46 and each layer can have a film thickness=666 nm. Each film layer is alternating spin coated. The poly(S-r-Se-DIB) is dissolved in chlorobenzene and the PVA is dissolved in water. The solvents must be "orthogonal" where the water-PVA solution cannot dissolve the underlying terpolymer and vice versa (i.e. the chlorobenzene-terpolymer does not dissolve PVA).

As used herein, the term "about" refers to plus or minus 10% of the referenced number.

Various modifications of the invention, in addition to those described herein, will be apparent to those skilled in the art from the foregoing description. Such modifications are also intended to fall within the scope of the invention. Each reference cited in the present application is incorporated herein by reference in its entirety.

Although there has been shown and described the preferred embodiment of the present invention, it will be readily apparent to those skilled in the art that modifications may be made thereto which do not exceed the scope of the invention. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures.

In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. An optical device comprising an optical polymer; wherein:
   the optical device is a Bragg grating, a phase mask, a waveguide grating router, a polymer interconnect, an echelle grating, a directional coupler, or a MachZehnder interferometer;
   the optical polymer is prepared from a polymer precursor;
   the polymer precursor is prepared by polymerizing a plurality of monomers of formula:

A-L-B

A comprises a vinylic group;
   L is a functional linker;
   B is a protecting group capable of being cleaved upon application of an external stimulus selected from the group consisting of application of an acid, a photoacid generator, heat, light irradiation, or a combination thereof;
   the polymer precursor is deprotected to remove the protecting group, thereby resulting in an irreversible change in refractive index, $\Delta_n$, and producing the optical polymer;
   $\Delta_n$ is greater than about 0.01.

2. The optical device of claim 1, wherein the polymer precursor is applied to a substrate using spin-coating.

3. The optical device of claim 1, wherein the polymer precursor is applied to a substrate and a photolithographic technique is used to produce a patterned optical device.

4. The optical device of claim 1, wherein A is a divinylic, multivinylic, or polyunsaturated group.

5. The optical device of claim 1, wherein A is a styrenic, acrylate, methacrylate, acrylamide, methacrylamide, or divinylbenzene.

6. The optical device of claim 1, wherein A is a vinylic group, and B is a tertbutyloxycarbonyl (BOC) or nitrobenzyl ether.

7. The optical device of claim 1, wherein L is a sulfide moiety, a selenium (Se) moiety, a tin (Sn) moiety, a titanium (Ti) moiety, a tellurium (Te) moiety, an aromatic moiety, a heteroaromatic-moiety, an aliphatic moiety, or an unsaturated moiety.

8. The optical device of claim 1, wherein:
   A is a styrenic, an acrylate, a methacrylate, an acrylamide, a methacrylamide, or a divinylbenzene; and
   L, is a sulfide moiety, a selenium (Se) moiety, a tin (Sn) moiety, a titanium (Ti) moiety, a tellurium (Te) moiety, an aromatic moiety, a heteroaromatic moiety, an aliphatic moiety, or an unsaturated moiety.

9. The optical device of claim 1, wherein a refractive index of the optical polymer is at least 0.01 greater than a refractive index of the polymer precursor.

10. The optical device of claim 1, wherein the monomer has the following structure:

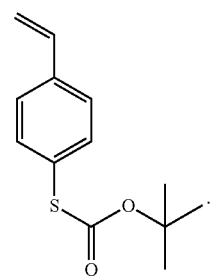 [SMILES: C=Cc1ccc(SC(=O)OC(C)(C)C)cc1]

* * * * *